(12) United States Patent
Camacho Gómez et al.

(10) Patent No.: US 9,447,095 B2
(45) Date of Patent: Sep. 20, 2016

(54) PYRIMIDINE DERIVATIVES AS PHOSPHODIESTERASE 10 INHIBITORS (PDE-10)

(71) Applicant: PALOBIOFARMA S.L., Mataró, Barcelona (ES)

(72) Inventors: Juan Camacho Gómez, Barcelona (ES); Julio Castro Palomino Laria, Barcelona (ES)

(73) Assignee: PALOBIOFARMA S.L., Barcelona (ES)

( * ) Notice: Subject to any disclaimer, the term of this patent is extended or adjusted under 35 U.S.C. 154(b) by 0 days.

(21) Appl. No.: 14/762,655

(22) PCT Filed: Jan. 24, 2014

(86) PCT No.: PCT/EP2014/051290
§ 371 (c)(1),
(2) Date: Jul. 22, 2015

(87) PCT Pub. No.: WO2014/114695
PCT Pub. Date: Jul. 31, 2014

(65) Prior Publication Data
US 2015/0336953 A1  Nov. 26, 2015

(30) Foreign Application Priority Data
Jan. 24, 2013  (ES) .................... 201330082

(51) Int. Cl.
| | | |
|---|---|---|
| C07D 403/04 | (2006.01) | |
| A61K 31/506 | (2006.01) | |
| C07D 471/04 | (2006.01) | |
| C07D 417/14 | (2006.01) | |
| C07D 405/14 | (2006.01) | |
| A61K 31/5377 | (2006.01) | |
| A61K 45/06 | (2006.01) | |
| C07D 401/14 | (2006.01) | |

(52) U.S. Cl.
CPC .......... *C07D 471/04* (2013.01); *A61K 31/506* (2013.01); *A61K 31/5377* (2013.01); *A61K 45/06* (2013.01); *C07D 401/14* (2013.01); *C07D 403/04* (2013.01); *C07D 405/14* (2013.01); *C07D 417/14* (2013.01)

(58) Field of Classification Search
CPC ........................... C07D 403/04; A61K 31/506
USPC ........................................... 544/324; 514/275
See application file for complete search history.

(56) References Cited

U.S. PATENT DOCUMENTS

| 8,343,970 B2 | 1/2013 | Cutshall et al. |
| 8,492,392 B2 | 7/2013 | Breslin et al. |
| 8,592,423 B2 | 11/2013 | Chaturvedula et al. |
| 8,859,543 B2 | 10/2014 | Bartolome-Nebreda et al. |
| 8,946,222 B2 | 2/2015 | Ripka et al. |
| 8,969,349 B2 | 3/2015 | Campbell et al. |
| 2008/0221103 A1 | 9/2008 | Sharma et al. |
| 2011/0224202 A1 | 9/2011 | Cutshall et al. |
| 2012/0065211 A1 | 3/2012 | Breslin et al. |
| 2012/0329792 A1 | 12/2012 | Bartolome-Nebreda et al. |
| 2013/0012511 A1 | 1/2013 | Schmidt et al. |
| 2013/0053308 A1 | 2/2013 | Camacho Gomez et al. |
| 2014/0256708 A1 | 9/2014 | Cox et al. |

FOREIGN PATENT DOCUMENTS

| WO | 2008110891 A1 | 9/2008 |
| WO | 2010128995 A1 | 11/2010 |
| WO | 2010150156 A1 | 12/2010 |
| WO | 2011119518 A1 | 9/2011 |
| WO | 2011121418 A1 | 10/2011 |
| WO | WO 2011/121418 A1 * | 10/2011 |
| WO | 2012177738 A1 | 12/2012 |
| WO | 2013052395 A1 | 4/2013 |

OTHER PUBLICATIONS

Layzer, Degenerative Diseases of the Nervous System, Cecil Textbook of Medicine, 20th Edition, vol. 2, pp. 2050-2057 (1996).*
Damasio, Alzheimer's Disease and Related Dementias, Cecil Textbook of Medicine, 20th Edition, vol. 2, pp. 1992-1996 (1996).*
Jordan, Nature Reviews: Drug Discovery, vol. 2, Issue 3, pp. 205-213 (2003).*
Fujishige et al., Cloning and Characterization of a Novel Human Phosphodiesterase That Hydrolyzes Both cAMP and cGMP (PDE10A), J. of Biological Chemistry, Jun. 25, 1999, vol. 274, No. 26, pp. 18438-18445.*

(Continued)

*Primary Examiner* — Deepak Rao
(74) *Attorney, Agent, or Firm* — Tristan A. Fuierer; Moore & Van Allen, PLLC

(57) ABSTRACT

The present invention relates to novel pyrimidine derivatives of formula (I)

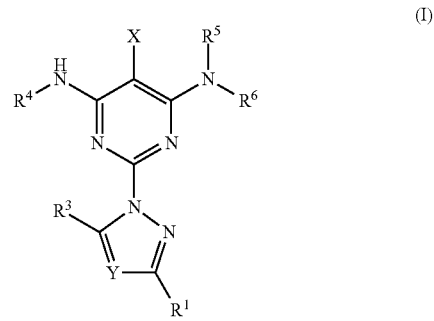

as inhibitors of the enzyme phosphodiesterase 10 (PDE-10), pharmaceutical compositions comprising an effective amount of these compounds and the use of the compounds for manufacturing a medicament for the treatment of pathological conditions or diseases that can improve by inhibition of the enzyme Phosphodiesterase 10 such as neurological, psychiatric, respiratory or metabolic diseases.

23 Claims, 1 Drawing Sheet

(56) References Cited

OTHER PUBLICATIONS

Bollen, Eva, et al; "Phosphoddiesterases in Neurodegenerative Disorders," IUBMB Life, 2012, pp. 965-970, vol. 64.
Chappie, Tom, et al.; "PDE10A inhibitors: An assessment of the current CNS drug discovery landscape," Current opinion in Drug Discover & Development, 2009, pp. 458-467, vol. 12.
Chappie, Thomas A., et al.; "Current Landscape of Phosphodiesterase 10A (PDE 10A) Inhibition," Journal of Medicinal Chemistry, 2012, pp. A-AG.
Desmond, Carly, et al.; "Phosphodiesterase inhibitors: new HD drugs entering trials soon," HD BUZZ, 2012, pp. 1-6.
Garcia-Ostra, Ana, et al.; "Phosphodiesterases as Therapeutic Targets for Alzheimer's Disease," American Chemical Society, 2012, pp. 832-844, vol. 3.
ClinicalTrials.gov; "Study Investigating the Safety and Tolerability of Multiple Doses of PF-02545920 in Subjects With Schizophtenia," Trial Record NCT00463372, 2007.
ClinicalTrials.gov; "Double Blind, Randomized, 3 Week Inpatient Study to Evaluate the Safety & Efficacy of PF-02545920 Compared With Placebo," Trial Record NCT00570063, 2007.
ClinicalTrials.gov; "An Inpatient Study of the Efficacy, Safety, and Tolerability of PF-02545920 in the Treatment of Acute Exacerbation of Schizophrenia," Trial Record NCT01175135, 2010.
ClinicalTrials.gov; "Effects of PF-02545920 on Ketamine-Induced Abnormal Prefrontal Brain Response to Associative Learning in Healthy Subjects," Trial Record NCT01244880, 2010.
International Search Report, Apr. 4, 2014.
Nishi, Akinori et al; "Distinct Roles of PDE4 and PDE10A in the Regulation of cAMP/PKA Signaling in the Striatum," The Journal of Neuroscience, 2008, pp. 10460-10471, vol. 28.
Giorgi, M. et al.; "PDE10A and PDE10A-dependent cAMP catabolism are dysregulated oppositely in striatum and nucleus accumbens after lesion of midbrain dopamine neurons in rat: A key step in parkinsonism physiopathology," Neurobiology of Disease, 2011, pp. 293-303, vol. 43.
Verhoest, Patrick R., et al.; "Discovery of a Novel Class of Phosphodiesterase 10A Inhibitors and Identification of Clinical Candidate 2-[4-(1-Methyl-4-pyridin-4-yl-1H-pyrazol-3-yl)-phenoxymethyl]-quinoline (PF-2545920) for the Treatment of Schizophrenia," J. Med. Chem., 2009, pp. 5188-5196, vol. 52.
Bender, Andrew T., et al.; "Cyclic Nucleotide Phosphodiesterases: Molecular Regulation to Clinical Use," Pharmacological Reviews, 2006, pp. 488-520, vol. 58.
Blokland, A., et al.; "PDE Inhibition and cognition enhancement," Expert Opinion on Therapeutic Patients, 2012, pp. 349-354, vol. 22.
Francis, Sharron H., et al.; "Mammalian Cyclic Nucleotide Phosphodiesterases: Molecular Mechanisms and Physiological Functions," Physiol Rev., 2011, pp. 651-690, vol. 91.
Giampà, Carmela, et al.; "Inhibition of the Striatal Specific Phosphodiesterase PDE10A Ameliorates Striatal and Cortical Pathology in R6/2 Mouse Model of Huntington's Disease," PLoS ONE, 2010, pp. 1-14, vol. 5.
Halene, Tobias, et al.; "Inhibitors in psychiatry—future options for dementia, depression and schizophrenia?", Drug Discovery Today, 2007, pp. 870-878, vol. 12.
Kelly, Michele P., et al.; "Phosphodiesterase 11A in brain is enriched in ventral hippocampus and deletion causes psychiatric disease-related phenotypes," PNAS, 2010, pp. 8457-8462, vol. 107.
Kleiman, Robin J., et al.; "Chronic Suppression of Phosphodiesterase 10A Alters Striatal Expression of Genes Responsible for Neurotransmitter Synthesis, Neurotransmission, and Signaling Pathways Implicated in Huntington's Disease," The Journal of Pharmacology and Experimental Therapeutics, 2011, pp. 64-76, vol. 336.
Rodefer, Joshua, et al.; "Selective phosphodiesterase inhibitors improve performance on the ED/ID cognitive task in rats," Neuropharmacology, 2011, pp. 1182-1190, vol. 62.
Schmidt, Christopher J.; "Phosphodiesterase inhibitors as potential cognition enhancing agents," Current Topics in Medicinal Chemistry, 2010, pp. 222-230, vol. 10.
Tian, Xia, et al.; "Phosphodiesterase 10A Upregulation Contributes to Pulmonary Vascular Remodeling," PLOS ONE, 2011, pp. 1-12, vol. 6.
Xu, Xing, et al.; "Phosphodiesterases in the central nervous system: Implications in mood and cognitive disorders," Handbook of Experimental Pharmacology, 2011, pp. 446-485, vol. 204.
Lakics, Viktor, et al.; "Quantitative comparison of phosphodiesterase mRNA distribution in juman brain and peripheral tissues," Neuropharmacology, 2010, pp. 367-374, vol. 59.
Menniti, Frank S., et al.; "Phosphodiesterase 10A inhibitors: A novel approach to the treatment of the symptoms of schizophrenia," Current Opinion in Investigational Drugs, 2007, pp. 54-59, vol. 8.
Rodefer, Joshua S., et al.; "PDE10A inhibition reverses subchronic PCP-induced deficits in attentional set-shifting in rats," European Journal of Neuroscience, 2005, pp. 1070-1076, vol. 21.
Siuciak, Judith A., et al.; "Behavioral characterization of mice deficient in the phosphodiesterase-10A (PDE10A) enzyme on a C57/B16N congenic background," Neuropharmacology, 2008, pp. 417-427, vol. 54.

\* cited by examiner

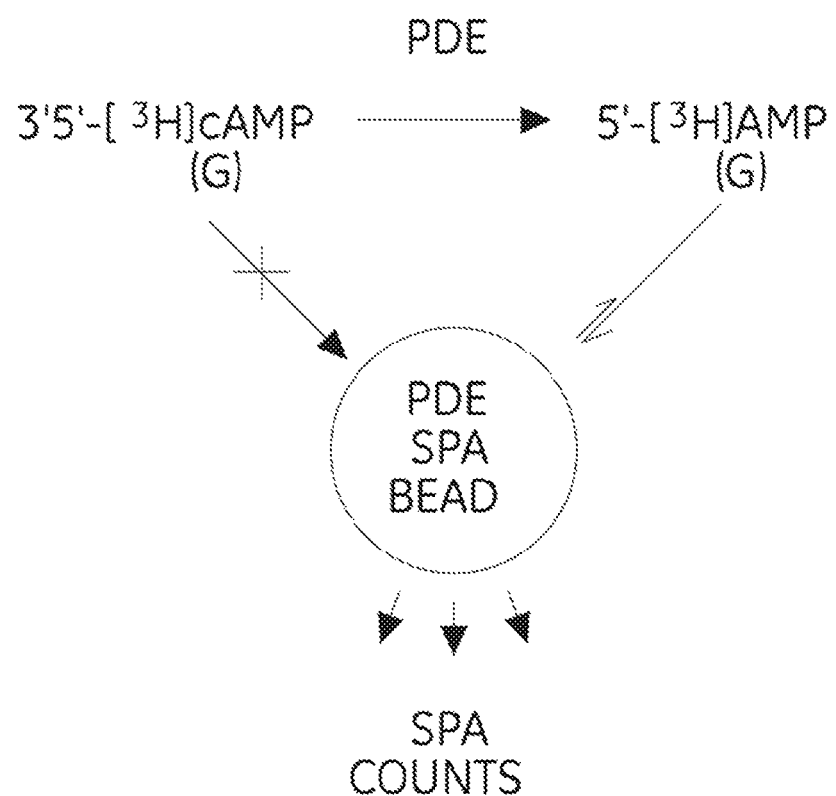

PYRIMIDINE DERIVATIVES AS PHOSPHODIESTERASE 10 INHIBITORS (PDE-10)

CROSS-REFERENCE TO RELATED APPLICATIONS

This application is filed under the provisions of 35 U.S.C. §371 and claims the priority of International Patent Application No. PCT/EP2014/051290 filed on 23 Jan. 2014 entitled "NEW PYRIMIDINE DERIVATIVES AS PHOSPHODIESTERASE 10 INHIBITORS (PDE-10)" in the name of Juan CAMACHO GÓMEZ, et al., which claims priority to Spanish Patent Application No. P201330082 filed on 24 Jan. 2013, both of which are hereby incorporated by reference herein in their entirety.

FIELD OF THE INVENTION

The present invention relates to novel pyrimidine derivatives conveniently substituted as inhibitors of the enzyme phosphodiesterase 10 (PDE-10). Other objectives of the present invention are to provide a procedure for preparing these compounds; pharmaceutical compositions comprising an effective amount of these compounds; the use of the compounds for manufacturing a medicament for the treatment of pathological conditions or diseases that can improve by inhibition of the enzyme Phosphodiesterase 10 such as neurological, psychiatric, respiratory or metabolic diseases.

STATE OF THE ART

Phosphodiesterases (PDEs) are a superfamily of enzymes that metabolize important intracellular messengers such as cyclic adenosine monophosphate (cAMP) and cyclic guanine monophosphate (cGMP). PDEs are encoded by 21 genes that are categorized into 11 different families based on the similarity of amino acid sequence, catalytic features and regulatory properties. Some PDEs specifically degrade cGMP (PDE5, 6 and 9), some specifically degrade cAMP (PDE4, 7 and 8) and some have a dual specificity (PDE1, 2, 3, 10 and 11) (Bender A T, Beavo J A. Cyclic nucleotide phosphodiesterases: molecular regulation to clinical use. Pharmacol Rev 2006; 58:488-520).

PDE families are divided into isoforms based on genetic encoding (for example, PDE4A-D) and isoform splicing (e.g., PDE4D1, PDE4D9); in total, more than 100 PDE isoforms have been identified. PDE isoforms have different location in cell tissue and subcellular levels, with a wide overlap being the rule rather than the exception. Thus, PDEs are essential for coordinating optimal concentrations of cAMP or cGMP in spatial and temporal dimensions; and inhibition of the PDE provides a means for the specific manipulation of signaling of cyclic nucleotide for therapeutic benefit (Francis S H, Blount M A, Corbin J D. Mammalian cyclic nucleotide phosphodiesterase: molecular mechanisms and physiological functions Physio Rev 2011; 91:651-90).

Cyclic nucleotides play a critical role in the regulation of synaptic plasticity, and therefore, inhibitors of the PDEs waked up considerable interest as treatments for cognitive dysfunction (Nalene T B, Siegel S J. PDE inhibitors in psychiatry—future options for dementia, depression and schizophrenia? Drug Discovery Today 2007; 12:870-8).

Cognitive function is the process by which the brain absorbs information and then analyzes this information in the current context to respond and plan for the future. These incredibly complex calculations are mediated by the continuous regulation of the synapses strength.

Inhibition of PDE-10 for the treatment of memory disorders in central nervous system diseases:

The knowledge of the location of PDE isoforms in different brain regions is essential in the design of inhibitors for various neuropsychiatric treatments, although it is only a first step. Several detailed and informative comparative analyses of PDE expression in the brain have been recently published (Lakics V, Karran E H, Boess F G, Quantitative comparison of phosphodiesterase mRNA distribution in human brain and peripheral tissues. Neuropharmacology 2010; 59:367-74; Xu Y, Zhang H T, O'Donnell J M. Phosphodiesterases in the central nervous system: implications in mood and cognitive disorders. Handb Exp Pharmacol 2011; 204:447-85).

PDE families have restricted distributions, including PDE10A, which is highly expressed in medium spiny neurons in the striatum. In the case of the PDE10A, its location has been an important clue and guide in the direction of the evaluation of PDE10A inhibitors for the treatment of memory problems in neuropsychiatric and neurodegenerative diseases such as schizophrenia and Huntington's disease (Phosphodiesterase 10A inhibitors: a novel approach to the treatment of the symptoms of schizophrenia. Curr Opin research Drugs 2007; 8:54-9; Carmela Giampa et to the; PLoSONE; 2010; Volume 5; Issue 10; Robin J. Kleiman et al; 2010; J. Pharmacol. Experimental Therapeutic; Vol. 336, No. 1).

Several recent publications show that PDE-10 inhibitors can reverse a motion deficit induced by inhibition of NMDA receptors in rats. This test can serve as a model of the deficit of executive function in patients with schizophrenia (Rodefer J S, Saland S K, Eckrich S J. Selective phosphodiesterase inhibitors improve performance on the ED/ID cognitive task in rats; Neuropharmacology 2012; 62:1182-1190).

Recently, inhibitors of PDE-10 have become a therapeutic target for research of central nervous system diseases, especially in relation to cognitive deficits associated with schizophrenia (Schmidt C J. Phosphodiesterase inhibitors as potential cognition enhancing agents; Curr Top Med Chem 2010; 10:222-30).

For example papaverine, a known Phosphodiesterase 10 inhibitor, has improved attention in the task change in rats which were affected by subchronic treatment of phenylcyclohexylpiperidine (PCP), a model of schizophrenia (Rodefer J, Murphy E, Baxter M; PDE10A inhibition reverses subchronic PCP-induced deficits in attentional set-shifting in rats. Eur J Neurosci, 2005, 21:1070-1076).

On the other hand, various models of knock-out mice have been useful to study the role of PDE10 in cognitive disorders (M. Kelly et al; PNAS; May 4, 2010; vol. 107; No. 18; 8457-8462). It was shown that PDE10A knock-out (KO) mice on a DBA1LacJ line require more training to achieve the performance of wild-type animals. In another study, KO PDE10A mice having a C57BL/6N background were also unable to reach the performance of wild-type mice (Siuciak, J. A., et al; Behavioral characterization of mice deficient in the phosphodiesterase-10A (PDE10A) enzyme on C57/BI6N congenic background. Neuropharmacology 2008, 54:417-427).

PDE10 inhibitors have been the most reported and patented for the treatment of cognitive deficits during the past two years (European Patent Office: www.epo.org). The comprehensive assessment of these publications reveals that PDE10 inhibition is mostly associated with the treatment of cognitive deficits in schizophrenia (Blokland et al; Expert Opin. Ther. Patents; 2012; 22(4):349-354).

There is a strong interest in the development of Phosphodiesterase-10 (PDE-10) inhibitors for the treatment of cognitive deficiencies. Preclinical studies have shown clearly beneficial effects of various PDE inhibitors in learning, memory and schizophrenia models. Currently, clinical trials are already ongoing with a PDE-10 inhibitor, Pfizer's PF-2545920 which is 2-[4-(1-methyl-4pyridin-4-yl-1H-pyrazol-3-yl)-phenoxymethyl]quinoline (Patrick R. Verhoest et al; J. Med. Chem. 2009, 52, 5188-5196).

PDE-10 inhibition for treatment of other diseases:

In addition to the mentioned role of this enzyme in diseases of the central nervous system, Phosphodiesterase 10 (PDE-10) is also expressed significantly in the lungs and recent articles show that its inhibition may be beneficial for the treatment of diseases such as hypertension or chronic obstructive pulmonary disease (COPD) (Pulmanseti et al; PLoS ONE; 2011; Vol. 6; Issue 4; 18136).

On the other hand, patent application WO 2011121418 describes structurally closest compounds, but being adenosine A2a antagonists, which are well known that diminish the intracellular cAMP levels. This patent application does not refers the use of said compounds as PDE10 inhibitors. Additionally, the compounds disclosed in WO 2011121418 differ from the compounds disclosed in the present patent application because the present compounds have a five membered heteroaryl ring comprising 2 nitrogen atoms a position Y which is either another nitrogen atom or a CR2 group, wherein R2 substituent represents aryl, heteroaryl, COOH or CONR$^8$R$^9$ group.

Related with the above, there are several studies demonstrating the role of adenosine A2a receptors and its antagonists over cAMP intracellular levels. For example, A. Nishi et al (*Distinct roles of PDE4 and PDE10A in the regulation of cAMP/PKA signaling in the striatum*, Journal of neuroscience, vol 28, no 42, 15-10-2008, pages 10460-10471) disclosed that adenosine A2a receptors stimulate the cAMP synthesis by enzyme adenyl cyclase. To evaluate the role of these receptors an assay was carried out demonstrating the action of adenosine A2a receptor antagonists and agonists on the effect induced by the PDE10 inhibitors, like papaverine. The outcomes show that adenosine A2a receptor antagonists attenuate the effect provoked by PDE10 inhibitors and the agonist enhanced said effect. Therefore, said assay makes evident the opposite effect of A2a antagonists and PDE10 inhibitors.

SUMMARY OF THE INVENTION

In one of its aspects, the present invention refers to pyrimidine derivatives of formula (I):

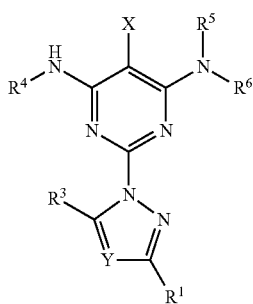

(I)

in which:

R$^1$ is selected from the group consisting of hydrogen, halogen, cycloalkyl and alkyl of three or four carbon atoms, linear or branched;

Y is selected from the group consisting of C—R$^2$ and nitrogen atom;

R$^2$ is selected from the group consisting of:

(a) an aryl or heteroaryl optionally substituted by one or more halogen atoms or by one or more cycloalkyl, hydroxy, lower alkoxy, lower alkylthio, amino, mono- or dialkylamino, alkoxyalkyl, hydroxycarbonyl and alkoxycarbonyl groups;

(b) an alkoxycarbonyl group of formula (—CO(R$^7$)), where R$^7$ independently represents a hydroxyl group or a [—N(R$^8$)(R$^9$)] group;

R$^8$ and R$^9$ are independently selected from the group consisting of hydrogen atom, cycloalkyl and alkyl from three to six carbon atoms, linear or branched and optionally substituted by halogen atoms or by an aryl or heterocyclic group;

or R$^8$ and R$^9$ may form, together with the nitrogen atom to which they are attached, a saturated 5- or 6-membered ring which optionally comprises a further a heteroatom selected from the group consisting of oxygen and nitrogen, being optionally substituted by a lower alkyl group;

R$^3$ is selected from the group consisting of hydrogen, halogen, cycloalkyl and lower alkyl, linear or branched optionally substituted by halogen atoms;

or R$^2$ and R$^3$ can form, together with the carbon atoms they are attached, six-membered aryl or heteroaryl ring, optionally substituted by one or more halogen atoms or by one or more groups selected from the group consisting of cycloalkyl, hydroxy, lower alkoxy, lower alkylthio, amino, mono- or dialkylamino, alkoxyalkyl, hydroxycarbonyl and alkoxycarbonyl;

X is selected from the group consisting of halogen atom and cyano group;

R$^4$, R$^5$ and R$^6$ are independently selected from the group consisting of:

(a) hydrogen atom;

(b) alkyl, cycloalkyl, or cycloalkylalkyl having a maximum of five carbon atoms, linear or branched, optionally substituted with one or more halogen atoms, methoxy groups, or a heteroaryl group, said heteroaryl group being optionally substituted with halogen atoms or lower alkyl groups;

(c) allyl or propargyl group optionally substituted by one or more halogen atoms or by one or more groups selected from the group consisting of cycloalkyl, hydroxy, lower alkoxy, lower (C$_1$-C$_8$) alkylthio, amino, mono- or dialkylamino, alkoxyalkyl, hydroxycarbonyl and alkoxycarbonyl; and (d) tetrahydropyranyl group;

or R$^5$ and R$^6$ can form, together with the atom of nitrogen to which they are attached, a pyrazole or triazole ring optionally substituted by halogen atoms.

Other aspects of the present invention are: a) pharmaceutically acceptable salts of said compounds; b) pharmaceutical compositions comprising an effective amount of said compounds; c) the use of said compounds in the manufacture of a medicament for the treatment of diseases which can improve by inhibition of Phosphodiesterase 10, such as Huntington's disease, schizophrenia, Parkinson's disease, Alzheimer's disease, depression, pulmonary hypertension, asthma and COPD; d) methods of treatment of diseases which can improve by inhibition of Phosphodiesterase 10, such as Huntington's disease, schizophrenia, Parkinson's disease, Alzheimer's disease, depression, pulmonary hypertension, asthma and COPD, said methods comprising the administration of the compounds of the invention to a subject in need thereof; and e) combination products that comprise a compound of formula (I) according to the invention, and another drug which is selected from drugs that are useful for the treatment of diseases of the central nervous system such as schizophrenia, Parkinson's disease, the disease of Huntington, Alzheimer's disease, or depression, or diseases as pulmonary hypertension, asthma and COPD.

DESCRIPTION OF THE FIGURE

The FIGURE shows the schematic representation of PDE [$^3$H] scintillation proximity assay (SPA).

DETAILED DESCRIPTION OF THE INVENTION

As used in the present document, the term lower alkyl includes radical linear or branched, optionally substituted having from 1 to 8, preferably 1 to 6 and more preferably from 1 to 4 carbon atoms.

Examples include methyl, ethyl, n-propyl, i-propyl, n-butyl, sec-butyl and tert-butyl, n-pentyl, 1-methylbutyl, 2-methylbutyl, isopentyl, 1-ethylpropyl, 1,1-dimethylpropyl, 1,2-dimethylpropyl, 2-ethylbutyl, 1-ethylbutyl, n-hexyl, 1,1-dimethylbutyl, 1,2-dimethylbutyl, 1,3-dimethylbutyl, 2,2-dimethylbutyl, 2,3-dimethylbutyl, 2-methylpentyl, 3-methylpentyl and iso-hexyl radicals.

As used in the present document, the term lower alkoxy includes radicals containing an oxy group and linear or branched, optionally, substituted having each alkyl moieties from 1 to 8, preferably 1 to 6 and more preferably from 1 to 4 carbon atoms.

Preferred alkoxy radicals include methoxy, ethoxy, n-propoxy, i-propoxy, n-butoxy, sec-butoxy, t-butoxy, trifluoromethoxy, difluoromethoxy, hydroxymethoxy, 2-hydroxyethoxy and 2-hydroxypropoxy.

As used in the present document, the term lower alkylthio includes radicals containing alkyl radicals optionally substituted linear or branched from 1 to 8, preferably 1-6 and more preferably from 1 to 4 carbon atoms.

Preferred alkylthio radicals include methylthio, ethylthio, n-propylthio, i-propylthio, n-butylthio, sec-butylthio, t-butylthio, trifluoromethylthio, difluoromethylthio, hydroxymethylthio, 2-hydroxyethylthio and 2-hydroxypropylthio.

As used in the present document, the term cyclic group includes, unless otherwise specified, carbocyclic and heterocyclic radicals. Cyclic radicals may contain one or more rings. The carbocyclic radical can be aromatic or alicyclic, e.g. cycloalkyl radical. Heterocyclic radicals include also heteroaryl radicals.

As used in the present document, the term aryl radical includes, typically, a monocyclic or polycyclic $C_5$-$C_{14}$ aryl radical as, for example, phenyl or naphthyl, anthranyl or phenanthryl, preferably phenyl. When an aryl has two or more substituents, said substituents can be the same or different.

As used in the present document, the term heteroaryl radical includes, typically, a ring system of 5 to 14 members comprising at least a heteroaromatic ring and that contains, at least, a heteroatom selected from O, S and N. A heteroaryl radical can be a single ring or two or more condensed rings, wherein at least one of the rings contains a heteroatom.

Examples include pyridyl, pyrazinyl, pyrimidinyl, pyridazinyl, furyl, oxadiazolyl, oxazolyl, imidazolyl, 1,3-thiazolyl, thiadiazolyl, thienyl, pyrrolyl, pyridinyl, benzo-1,3-thiazolyl, indolyl, indazolyl, purinyl, quinolyl, isoquinolyl, phthalazinyl, naphthiridinyl, quinoxalinyl, quinazolinyl, quinolizinyl, cinnolinyl, triazolyl, indolizinyl, indolinyl, isoindolinyl, isoindolyl, imidazolidinyl and pyrazolyl. Preferred radicals are optionally substituted pyridinyl, 1,3-thiazolyl and furanyl.

When a heteroaryl radical has two or more substituents, said substituents can be the same or different.

As used in the present document, some of the atoms, radical, moieties, chains or cycles present in the general structures of the invention are "optionally substituted". This means that these atoms, radicals, moieties, chains or cycles may be unsubstituted or replaced in any position by one or more, for example 1, 2, 3 or 4 substituents, in which the hydrogen atoms attached to said unsubstituted atoms, radicals, moieties, chains or cycles are replaced by chemically acceptable atoms, radicals, moieties, chains or cycles. When two or more substituents are present, each substituent can be the same or different.

As used in the present document, the term halogen atom includes chlorine, fluorine, bromine and iodine atoms, preferably fluorine, chlorine and bromine, more preferably bromine and chlorine atoms. The term halo, when used as a prefix has the same meaning.

As used in the present document, the term pharmaceutically acceptable salt encompasses salts with a pharmaceutically acceptable acid or base. Pharmaceutically acceptable acids include inorganic acids, such as hydrochloric, sulphuric, phosphoric, diphosphoric, hydrobromic, hydroiodic and nitrate acids, and organic acids, such as citric, maleic, malic, mandelic, ascorbic, oxalic, succinic, tartaric, acetic, methanesulfonic, ethanesulfonic, benzenesulfonic and p-toluenosulfonic acids. Pharmaceutically acceptable bases include hydroxides of alkali metals (e.g. sodium or potassium), alkaline-earth metals (for example, calcium or magnesium) and organic bases (for example, alkylamines, arylalkyilamines and heterocyclic amines).

Other preferred salts according to the invention are quaternary ammonium compounds in which an equivalent of an anion (X—) is associated with the positive charge of the N atom. X— may be an anion of diverse mineral acids such as for example, chloride, bromide, iodide, sulfate, nitrate, phosphate, or an anion of an organic acid, such as acetate, maleate, fumarate, citrate, oxalate, succinate, tartrate, malate, mandelate, trifluoracetate, methanesulfonate and p-toluenesulfonate. X— is preferably an anion selected from chloride, bromide, iodide, sulfate, nitrate, acetate, maleate, oxalate, succinate and trifluoracetate. More preferably X— is chloride, bromide, trifluoracetate or methanesulfonate.

According to a preferred embodiment of the present invention, in the compounds of formula (I), the $R^1$, $R^3$, $R^4$ and $R^5$ groups represent a hydrogen atom, X represents a bromine atom and Y represents a nitrogen atom.

According to a still more preferred embodiment of the present invention, in the compounds of formula (I), the $R^1$, $R^3$, $R^4$ and $R^5$ groups represent a hydrogen atom, X represents a bromine atom, Y represents a nitrogen atom and $R^6$ represents a propargyl or alkyl groups optionally substituted with a five-membered heteroaryl ring which in turn can be optionally substituted by a lower alkyl group.

According to another preferred embodiment of the present invention, in the compounds of formula (I), the $R^1$, $R^4$ and $R^5$ groups represent a hydrogen atom, X represents a bromine atom, Y represents a C—$R^2$ moiety, and the $R^2$ and $R^3$ groups form, together with the carbon atoms to which they are attached, a pyridine or phenyl ring.

According to more preferred embodiment of the present invention, in the compounds of formula (I), the $R^1$, $R^4$ and $R^5$ groups represent a hydrogen atom, X represents a bromine atom, Y represents an $C-R^2$ moiety, the $R^2$ and $R^3$ groups form, together with the carbon atoms to which they are attached phenyl or pyridine ring, and $R^6$ represents a propargyl or a lower alkyl optionally substituted by a methoxy group or by a five-membered heteroaryl ring which in turn can be optionally substituted by a lower alkyl group.

According to another preferred embodiment of the present invention, in the compounds of formula (I), the $R^1$, $R^3$, $R^4$ and $R^5$ groups represent a hydrogen atom, X represents a bromine atom, Y represents a $C-R^2$ moiety, and the $R^2$ group represents a 6 membered heteroaryl ring optionally substituted by halogen atoms.

According to a more preferred embodiment of the present invention, in the compounds of formula (I), $R^4$ represents a hydrogen atom.

According to another embodiment of the present invention, in the compounds of formula (I), $R^1$, $R^3$ and $R^5$ represent a hydrogen atom, X represents a bromine atom and Y represents a nitrogen atom.

According to another preferred embodiment of the present invention, in the compounds of formula (I), $R^6$ is selected from the group consisting of alkyl, cycloalkylalkyl and alkylcycloalkyl, optionally substituted with a methoxy group or a heteroaryl group, which in turn can be optionally substituted by a lower alkyl group.

According to another preferred embodiment of the present invention, in the compounds of formula (I), $R^6$ is selected from the group consisting of ethyl, propyl, and cyclopropylmethyl, all of them being optionally substituted by a methoxy group or a five-membered heteroaryl group, which in turn can be optionally substituted by one or more methyl groups.

According to another preferred embodiment of the present invention, in the compounds of formula (I), $R^6$ is selected from the group consisting of allyl, propargyl and tetrahydropyranyl, all of them being optionally substituted by a linear or branched alkyl group having a maximum of 3 carbon atoms.

According to another embodiment of the present invention, in the compounds of formula (I), $R^1$, $R^3$ and $R^5$ represent a hydrogen atom, X represents a bromine atom, Y represents a $C-R^2$ moiety and $R^2$ represents a heteroaryl group optionally substituted by halogen atoms.

According to another preferred embodiment of the present invention, in the compounds of formula (I), Y is $C-R^2$, wherein $R^2$ is selected from the group consisting of pyridine, quinoline, pyrimidine and pyrazine all of them being optionally substituted by halogen atoms.

According to another preferred embodiment of the present invention, in the compounds of formula (I), $R^6$ is selected from the group consisting of alkyl, cycloalkylalkyl and alkylcycloalkyl groups, all of them being optionally substituted with a methoxy group or with a heteroaryl group which, in turn, is optionally substituted by a lower alkyl group.

According to another preferred embodiment of the present invention, in the compounds of formula (I), $R^6$ is selected from the group consisting in ethyl, propyl, and cyclopropylmethyl, all of them being optionally substituted by a methoxy group or by a five-membered heteroaryl group optionally substituted by one or more methyl groups.

According to another preferred embodiment of the present invention, in the compounds of formula (I), $R^6$ is selected from the group consisting of allyl, propargyl and tetrahydropyranyl groups optionally substituted by halogen atoms.

According to another embodiment of the present invention, in the compounds of formula (I), $R^1$ and $R^5$ represent a hydrogen atom, X represents a bromine atom, Y represents a $C-R^2$ moiety, and $R^2$ and $R^3$ form, together with the carbon atoms to which they are attached, an optionally substituted aryl or heteroaryl ring.

According to another preferred embodiment of the present invention, in the compounds of formula (I), $R^2$ and $R^3$ form, together with the carbon atoms to which they are attached, a phenyl ring or a pyridine ring optionally substituted by halogen atoms.

According to another preferred embodiment of the present invention, in the compounds of formula (I), $R^6$ is selected from the group consisting of alkyl, cycloalkylalkyl and alkylcycloalkyl optionally substituted with a methoxy group or a heteroaryl group which, in turn, is optionally substituted by a lower alkyl group.

According to another preferred embodiment of the present invention, in the compounds of formula (I), $R^6$ is selected from the group consisting of ethyl, propyl and cyclopropylmethyl, optionally substituted by a methoxy group or by a 5-membered heteroaryl ring optionally substituted by one or more methyl groups.

According to another preferred embodiment of the present invention, in the compounds of formula (I), $R^6$ is selected from the group consisting of optionally substituted allyl, propargyl, and tetrahydropyranyl.

According to another embodiment of the present invention, in the compounds of formula (I), $R^1$ and $R^5$ represent a hydrogen atom, X represents a bromine atom, Y represents a $C-R^2$ moiety, $R^2$ and $R^3$ form, together with the carbon atoms to which are attached, a phenyl ring or a pyridine ring, and $R^6$ is selected from the group consisting of ethyl, propyl and cyclopropylmethyl optionally substituted by a thiazole ring optionally substituted by one or more methyl groups.

According to another preferred embodiment of the present invention, in the compounds of formula (I), $R^1$, $R^3$ and $R^5$ represent a hydrogen atom, X represents a bromine atom, Y represents nitrogen atom, and $R^6$ is selected from the group consisting of ethyl, propyl, propargyl, cyclopropylmethyl optionally substituted by a thiazolyl ring, which in turn is optionally substituted by one or more methyl groups.

According to another embodiment of the present invention, in the compounds of formula (I), $R^1$, $R^3$, $R^4$ and $R^5$ represent a hydrogen atom, X represents a bromine atom and Y represents a nitrogen atom.

According to another embodiment of the present invention, in the compounds of formula (I), $R^1$, $R^3$, $R^4$ and $R^5$ represent a hydrogen atom, X represents a bromine atom, Y represents a nitrogen atom, and $R^6$ is selected from the group consisting of alkyl, cycloalkylalkyl and alkylcycloalkyl, optionally substituted with a methoxy group or a heteroaryl group, which in turn can be optionally substituted by a lower alkyl group; preferably, $R^6$ is selected from the group consisting of ethyl, propyl, and cyclopropylmethyl, all of them being optionally substituted by a methoxy group or a five-membered heteroaryl group, which in turn can be optionally substituted by one or more methyl groups.

According to another embodiment of the present invention, in the compounds of formula (I), $R^1$, $R^3$, $R^4$ and $R^5$ represent a hydrogen atom, X represents a bromine atom, Y represents a nitrogen atom, and $R^6$ is selected from the group consisting of allyl, propargyl and tetrahydropyranyl, all them being optionally substituted by a linear or branched alkyl group having a maximum of 3 carbon atoms.

According to another embodiment of the present invention, in the compounds of formula (I), $R^1$, $R^3$, $R^4$ and $R^5$ represent a hydrogen atom, X represents a bromine atom, Y represents an C—$R^2$ moiety and $R^2$ represents a heteroaryl group optionally substituted by halogen atoms; preferably $R^2$ is selected from the group consisting of pyridine, quinoline, pyrimidine and pyrazine all of them being optionally substituted by halogen atoms.

According to another embodiment of the present invention, in the compounds of formula (I), $R^1$, $R^3$, $R^4$ and $R^5$ represent a hydrogen atom, X represents a bromine atom, Y represents an C—$R^2$ moiety, $R^2$ is selected from the group consisting of pyridine, quinoline, pyrimidine and pyrazine all of them being optionally substituted by halogen atoms, and $R^6$ is selected from the group consisting of alkyl, cycloalkylalkyl and alkylcycloalkyl groups, all of them being optionally substituted with a methoxy group or with a heteroaryl group which, in turn, is optionally substituted by a lower alkyl group; preferably $R^6$ is selected from the group consisting in ethyl, propyl, and cyclopropylmethyl, all of them being optionally substituted by a methoxy group or by a five-membered heteroaryl group optionally substituted by one or more methyl groups.

According to another embodiment of the present invention, in the compounds of formula (I), $R^1$, $R^3$, $R^4$ and $R^5$ represent a hydrogen atom, X represents a bromine atom, Y represents an C—$R^2$ moiety, $R^2$ is selected from the group consisting of pyridine, quinoline, pyrimidine and pyrazine all of them being optionally substituted by halogen atoms, and $R^6$ is selected from the group consisting of allyl, propargyl and tetrahydropyranyl groups optionally substituted by halogen atoms.

According to another embodiment of the present invention, in the compounds of formula (I), $R^1$, $R^4$ and $R^5$ represent a hydrogen atom, X represents a bromine atom, Y represents a C—$R^2$ moiety, and $R^2$ and $R^3$ form, together with the carbon atoms to which they are attached, an optionally substituted aryl or heteroaryl ring.

According to another embodiment of the present invention, in the compounds of formula (I), $R^1$, $R^4$ and $R^5$ represent a hydrogen atom, X represents a bromine atom, Y represents a C—$R^2$ moiety, and $R^2$ and $R^3$ form, together with the carbon atoms to which they are attached, an optionally substituted aryl or heteroaryl ring; preferably $R^2$ and $R^3$ form, together with the carbon atoms to which they are attached, a phenyl ring or a pyridine ring optionally substituted by halogen atoms.

According to another embodiment of the present invention, in the compounds of formula (I), $R^1$, $R^4$ and $R^5$ represent a hydrogen atom, X represents a bromine atom, Y represents a C—$R^2$ moiety, $R^2$ and $R^3$ form, together with the carbon atoms to which they are attached, a phenyl ring or a pyridine ring optionally substituted by halogen atoms, and $R^6$ is selected from the group consisting of alkyl, cycloalkylalkyl and alkylcycloalkyl optionally substituted with a methoxy group or a heteroaryl group which, in turn, is optionally substituted by a lower alkyl group; preferably $R^6$ is selected from the group consisting of ethyl, propyl and cyclopropylmethyl, optionally substituted by a methoxy group or by a 5-membered heteroaryl ring optionally substituted by one or more methyl groups.

According to another embodiment of the present invention, in the compounds of formula (I), $R^1$, $R^4$ and $R^5$ represent a hydrogen atom, X represents an bromine atom, Y represents a C—$R^2$ moiety, $R^2$ and $R^3$ form, together with the carbon atoms to which they are attached, a phenyl ring or a pyridine ring optionally substituted by halogen atoms, and $R^6$ is selected from the group consisting of optionally substituted allyl, propargyl, and tetrahydropyranyl.

According to another embodiment of the present invention, in the compounds of formula (I), $R^1$, $R^4$ and $R^5$ represent a hydrogen atom, X represents a bromine atom, Y represents a C—$R^2$ moiety, $R^2$ and $R^3$ form, together with the carbon atoms to which are attached, a phenyl ring or a pyridine ring, and $R^6$ is selected from the group consisting of ethyl, propyl and cyclopropylmethyl optionally substituted by a thiazole ring optionally substituted by one or more methyl groups.

According to another preferred embodiment of the present invention, in the compounds of formula (I), $R^1$, $R^3$, $R^4$ and $R^5$ represent a hydrogen atom, X represents a bromine atom, Y represents nitrogen atom, and $R^6$ is selected from the group consisting of ethyl, propyl, propargyl, cyclopropylmethyl optionally substituted by a thiazolyl ring, which in turn is optionally substituted by one or more methyl groups.

According to a preferred embodiment of the present invention, in the compounds of formula (I) $R^1$, $R^3$, $R^4$ and $R^5$ represent a hydrogen atom, X represents a bromine atom, Y represents a nitrogen atom, and $R^6$ is selected from the group consisting of ethyl, propyl, and cyclopropylmethyl, all of them being optionally substituted by a methoxy group or a five-membered heteroaryl group, which in turn can be optionally substituted by one or more methyl groups, and allyl, propargyl and tetrahydropyranyl, all them being optionally substituted by a linear or branched alkyl group having a maximum of 3 carbon atoms.

Particular individual compounds of the invention include, among others:

5-bromo-$N^4$-(cyclopropylmethyl)-2-(1H-indazol-1-yl)pyrimidine-4,6-diamine;

5-bromo-$N^4$-ethyl-2-(1H-indazol-1-yl)pyrimidine-4,6-diamine;

5-bromo-2-(1H-indazol-1-yl)-$N^4$-(prop-2-ynyl)pyrimidine-4,6-diamine;

5-bromo-2-(1H-indazol-1-yl)-6-(1H-pyrazol-1-yl)pyrimidin-4-amine;

$N^4$-[(1H-benzo[d]imidazol-2-yl)methyl]-5-bromo-2-(1H-indazol-1-yl)pyrimidine-4,6-diamine;

5-bromo-2-(1H-indazol-1-yl)-$N^4$-[(2-methylthiazol-4-yl)methyl]pyrimidine-4,6-diamine;

5-bromo-$N^4$-(tetrahydro-2H-pyran-4-yl)-2-(1H-indazol-1-yl)pyrimidine-4,6-diamine;

5-bromo-2-(1H-indazol-1-yl)-$N^4$-[(1-methyl-1H-pyrazol-4-yl)methyl]pyrimidine-4,6-diamine;

5-bromo-2-(1H-indazol-1-yl)-$N^4$-[(thiazol-5-yl)methyl]pyrimidine-4,6-diamine;

5-bromo-2-(1H-indazol-1-yl)-$N^4$-[(4-methylthiazol-5-yl)methyl]pyrimidine-4,6-diamine;

5-bromo-2-(1H-indazol-1-yl)-$N^4$-(2-methoxyethyl)pyrimidine-4,6-diamine;

5-bromo-$N^4$-[(4-methylthiazol-5-yl)methyl]-2-(1H-pyrazol-1-yl)pyrimidine-4,6-diamine;

5-bromo-$N^4$-(2-methoxyethyl)-2-(1H-pyrazol-1-yl)pyrimidine-4,6-diamine;

$N^4$-[(1H-benzo[d]imidazol-2-yl)methyl]-5-bromo-2-(1H-pyrazol-1-yl)pyrimidine-4,6-diamine;

5-bromo-$N^4$-(prop-2-ynyl)-2-[4-(pyridin-4-yl)-1H-pyrazol-1-yl]pyrimidine-4,6-diamine;

5-bromo-2-(4-(pyridin-4-yl)-1H-pyrazol-1-yl)-$N^4$-[(thiazol-5-yl)methyl]pyrimidine-4,6-diamine;

5-bromo-$N^4$-(prop-2-ynyl)-2-[4-(pyridin-2-yl)-1H-pyrazol-1-yl]pyrimidine-4,6-diamine;

5-bromo-N⁴-(cyclopropylmethyl)-2-[4-(pyridin-2-yl)-1H-pyrazol-1-yl]pyrimidine-4,6-diamine;
5-bromo-N⁴-[(4-methylthiazol-5-yl)methyl]-2-(4-(pyridin-2-yl)-1H-pyrazol-1-yl)pyrimidine-4,6-diamine;
5-bromo-2-[4-(pyridin-2-yl)-1H-pyrazol-1-yl]-N⁴-[(thiazol-5-yl)methyl]pyrimidine-4,6-diamine;
5-bromo-N⁴-(2-methoxyethyl)-2-[4-(pyridin-2-yl)-1H-pyrazol-1-yl]pyrimidine-4,6-diamine;
5-bromo-N⁴-(prop-2-ynyl)-2-[4-(quinolin-2-yl)-1H-pyrazol-1-yl]pyrimidine-4,6-diamine;
5-bromo-N⁴-(tetrahydro-2H-pyran-4-yl)-2-[4-(quinolin-2-yl)-1H-pyrazol-1-yl]pyrimidine-4,6-diamine;
5-bromo-N⁴-[(2-methylthiazol-4-yl)methyl]-2-[4-(quinolin-2-yl)-1H-pyrazol-1-yl]pyrimidine-4,6-diamine;
5-bromo-N⁴-[(4-methylthiazol-5-yl)methyl]-2-[4-(quinolin-2-yl)-1H-pyrazol-1-yl]pyrimidine-4,6-diamine;
5-bromo-N⁴-ethyl-2-(4-phenyl-1H-pyrazol-1-yl)pyrimidine-4,6-diamine;
5-bromo-2-[4-(4-chlorophenyl)-1H-pyrazol-1-yl]-N⁴-ethyl-pyrimidine-4,6-diamine;
5-bromo-2-[4-(4-chlorophenyl)-1H-pyrazol-1-yl]-N⁴-(prop-2-ynyl)pyrimidine-4,6-diamine;
5-bromo-N⁴-[(4-methylthiazol-5-yl)methyl]-2-[4-(pyrazin-2-yl)-1H-pyrazol-1-yl]pyrimidine-4,6-diamine;
5-bromo-N⁴-(prop-2-ynyl)-2-[4-(pyrazin-2-yl)-1H-pyrazol-1-yl]pyrimidine-4,6-diamine;
5-bromo-N⁴-(prop-2-ynyl)-2-(1H-pyrazolo[3,4-b]pyridin-1-yl)pyrimidine-4,6-diamine;
5-bromo-N⁴-[(4-methylthiazol-5-yl)methyl]-2-(1H-pyrazolo[3,4-b]pyridin-1-yl)pyrimidine-4,6-diamine;
5-bromo-N⁴-(prop-2-ynyl)-2-(1H-pyrazolo[3,4-c]pyridin-1-yl)pyrimidine-4,6-diamine;
5-bromo-N⁴-[(4-methylthiazol-5-yl)methyl]-2-(1H-pyrazolo[3,4-c]pyridin-1-yl)pyrimidine-4,6-diamine;
5-bromo-N⁴-(cyclopropylmethyl)-2-(1H-pyrazolo[3,4-c]pyridin-1-yl)pyrimidine-4,6-diamine;
5-bromo-2-(1H-pyrazolo[3,4-c]pyridin-1-yl)-N⁴-[(thiazol-5-yl)methyl]pyrimidine-4,6-diamine;
5-bromo-N⁴-(2-methoxyethyl)-2-(1H-pyrazolo[3,4-c]pyridin-1-yl)pyrimidine-4,6-diamine;
5-bromo-N⁴-(prop-2-ynyl)-2-(1H-pyrazolo[4,3-c]pyridin-1-yl)pyrimidine-4,6-diamine;
5-bromo-N⁴-[(4-methylthiazol-5-yl)methyl]-2-(1H-pyrazolo[4,3-c]pyridin-1-yl)pyrimidine-4,6-diamine;
5-bromo-N⁴-(prop-2-ynyl)-2-(1H-pyrazolo[4,3-b]pyridin-1-yl)pyrimidine-4,6-diamine;
5-bromo-N⁴-[(4-methylthiazol-5-yl)methyl]-2-(1H-pyrazolo[4,3-b]pyridin-1-yl)pyrimidine-4,6-diamine;
5-bromo-N⁴-(prop-2-ynyl)-2-(1H-1,2,4-triazol-1-yl)pyrimidine-4,6-diamine;
5-bromo-N⁴-[(4-methylthiazol-5-yl)methyl]-2-(1H-1,2,4-triazol-1-yl)pyrimidine-4,6-diamine;
5-bromo-N⁴-(2-methoxyethyl)-2-(1H-1,2,4-triazol-1-yl)pyrimidine-4,6-diamine;
5-bromo-N⁴-[(thiazol-5-yl)methyl]-2-(1H-1,2,4-triazol-1-yl)pyrimidine-4,6-diamine;
5-bromo-N⁴-(cyclopropylmethyl)-2-(1H-1,2,4-triazol-1-yl)pyrimidine-4,6-diamine;
1-[4-amino-5-bromo-6-(prop-2-ynylamino)pyrimidin-2-yl]-1H-pyrazole-4-carboxylic acid;
1-[4-amino-5-bromo-6-(ethylamino)pyrimidin-2-yl]-1H-pyrazole-4-carboxylic acid;
1-{4-[(4-methylthiazol-5-yl)methylamino]-6-amino-5-bromopyrimidin-2-yl}-1H-pyrazole-4-carboxylic acid;
{1-[4-amino-5-bromo-6-(ethylamino)pyrimidin-2-yl]-1H-pyrazol-4-yl}(morpholino)methanone;
5-bromo-6-(1H-pyrazol-1-yl)-2-[4-(pyridin-4-yl)-1H-pyrazol-1-yl]pyrimidin-4-amine;
5-bromo-6-(1H-pyrazol-1-yl)-2-[4-(pyridin-2-yl)-1H-pyrazol-1-yl]pyrimidin-4-amine;
5-bromo-2-[4-(pyrazin-2-yl)-1H-pyrazol-1-yl]-6-(1H-pyrazol-1-yl)pyrimidin-4-amine;
5-bromo-6-(1H-pyrazol-1-yl)-2-(1H-1,2,4-triazol-1-yl)pyrimidin-4-amine;
1-[4-(2-methoxyethylamino)-6-amino-5-bromopyrimidin-2-yl]-1H-pyrazole-4-carboxylic acid;
1-[4-amino-5-bromo-6-(cyclopropylmethylamino)pyrimidin-2-yl]-1H-pyrazole-4-carboxylic acid;
1-[4-amino-5-bromo-6-(isopropylamino)pyrimidin-2-yl]-1H-pyrazole-4-carboxylic acid;
5-bromo-N⁴-ethyl-2-[4-(pyridin-2-yl)-1H-pyrazol-1-yl]pyrimidine-4,6-diamine;
5-bromo-N⁴-ethyl-2-[4-(pyrimidin-4-yl)-1H-pyrazol-1-yl]pyrimidine-4,6-diamine;
5-bromo-N⁴-ethyl-2-[4-(quinolin-2-yl)-1H-pyrazol-1-yl]pyrimidine-4,6-diamine;
5-chloro-N⁴-ethyl-2-[4-(pyridin-2-yl)-1H-pyrazol-1-yl]pyrimidine-4,6-diamine;
5-chloro-N⁴-ethyl-2-(1H-indazol-1-yl)pyrimidine-4,6-diamine;
5-chloro-N⁴-ethyl-2-(5-fluoro-1H-indazol-1-yl)pyrimidine-4,6-diamine;
5-bromo-N⁴-ethyl-2-(1H-indazol-1-yl)-N⁶-(prop-2-ynyl)pyrimidine-4,6-diamine;
5-bromo-N⁴-(cyclopropylmethyl)-2-(1H-indazol-1-yl)-N⁶-(prop-2-ynyl)pyrimidine-4,6-diamine;
5-bromo-N⁴-(tetrahydro-2H-pyran-4-yl)-2-(1H-indazol-1-yl)-N⁶-(prop-2-ynyl)pyrimidine-4,6-diamine;
N⁴-[(1H-benzo[d]imidazol-2-yl)methyl]-5-bromo-2-(1H-indazol-1-yl)-N⁶-(prop-2-ynyl)pyrimidine-4,6-diamine;
5-bromo-N⁴-ethyl-N⁶-(prop-2-ynyl)-2-[4-(pyridin-2-yl)-1H-pyrazol-1-yl]pyrimidine-4,6-diamine;
5-bromo-N⁴-(cyclopropylmethyl)-N⁶-(prop-2-ynyl)-2-[4-(pyridin-2-yl)-1H-pyrazol-1-yl]pyrimidine-4,6-diamine;
5-bromo-N⁴-(tetrahydro-2H-pyran-4-yl)-N⁶-(prop-2-ynyl)-2-[4-(pyridin-2-yl)-1H-pyrazol-1-yl]pyrimidine-4,6-diamine;
N⁴-[(1H-benzo[d]imidazol-2-yl)methyl]-5-bromo-N⁶-(prop-2-ynyl)-2-[4-(pyridin-2-yl)-1H-pyrazol-1-yl]pyrimidine-4,6-diamine;
5-bromo-N⁴-ethyl-N⁶-(prop-2-ynyl)-2-[4-(pyrimidin-4-yl)-1H-pyrazol-1-yl]pyrimidine-4,6-diamine;
5-bromo-N⁴-(cyclopropylmethyl)-N⁶-ethyl-2-[4-(pyrimidin-4-yl)-1H-pyrazol-1-yl]pyrimidine-4,6-diamine;
5-bromo-N⁴-ethyl-N⁶-(tetrahydro-2H-pyran-4-yl)-2-[4-(pyrimidin-4-yl)-1H-pyrazol-1-yl]pyrimidine-4,6-diamine; and
N⁴-[(1H-benzo[d]imidazol-2-yl)methyl]-5-bromo-N⁶-ethyl-2-[4-(pyrimidin-4-yl)-1H-pyrazol-1-yl]pyrimidine-4,6-diamine.

The compounds of this invention can be prepared by using the procedures described below. To facilitate the description of the procedures concrete examples have been used, but they do not restrict the scope of the present invention.

When R⁴ represents a hydrogen atom in the compounds of formula (I), the corresponding derivatives have been synthesized through the sequence of reactions represented in reaction Scheme 1.

Scheme 1

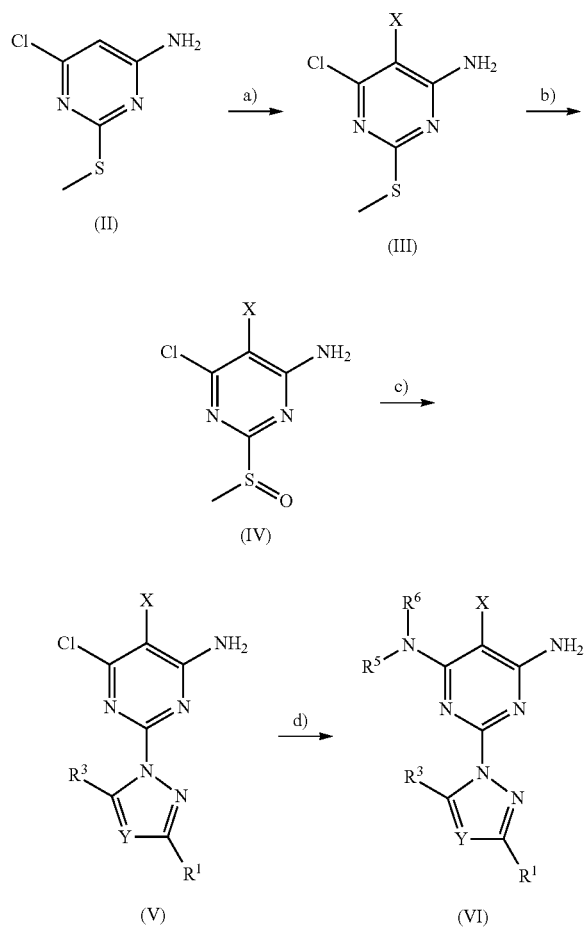

Reagents and conditions: R⁴ = H; Y = N or C—R²; (a) X = Cl, Br or I, N-chloro-, N-bromo- or N-iodosuccinimide (1.05 eq), DCM, RT; (b) m-chloroperbenzoic acid (1.1 eq), DCM, RT; (c) pyrazole or indazole derivative (1 eq), cesium carbonate, DMF, RT; (d) amine (4 eq), cesium carbonate, DMSO, 80° C.

Firstly, to a commercially available pyrimidine derivative of formula (II), a halogen atom is introduced in position 5 of the pyrimidine ring using the corresponding halo-succinimide derivative to give the derivatives of formula (III). Monoxidation of the thiomethyl group bonded at position 2 of the pyrimidine ring of compound (III) is subsequently performed with meta-chloroperbenzoic acid obtaining the derivatives of formula (IV).

The nucleophilic substitution of the sulfinyl group in the derivatives of formula (IV) by commercially available pyrazole, triazole, indazole or azaindazole derivatives affords the intermediates of formula (V). Finally, the chlorine atom in position 6 of the pyrimidine ring of these intermediates of formula (V) can be substituted by primary or secondary amines at 80° C. in DMSO as solvent to yield compounds of formula (VI), which constitute an example of the type of compounds claimed by the present invention.

The reaction sequence shown in Scheme 2 does also give compounds as previously described, only by changing the sequence in which the substituents are introduced, using for this purpose the same reactions as described above in Scheme 1.

Scheme 2

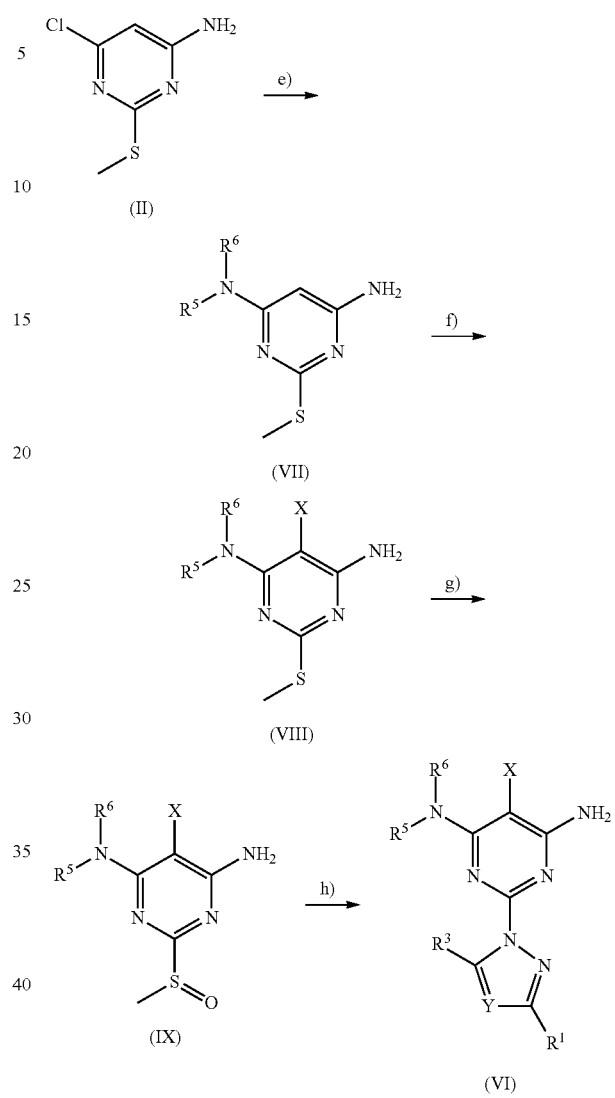

Reagents and conditions: R⁴ = H; Y = N or C—R²; (e) amine (6 eq), cesium carbonate, DMSO, 80° C.; (f) x = Cl, Br or I, N-chloro-, N-bromo- or N-iodosuccinimide (1.05 eq), DCM, RT; (g) m-chloroperbenzoic acid (1.1 eq), DCM, RT; (h) pyrazole or indazole derivative (1 eq), cesium carbonate, DMSO.

The procedures described in Reaction Scheme 3 can be used to synthesize pyrimidine derivatives, in which R⁴, R⁵ and R⁶ respectively are not a hydrogen atom.

Scheme 3

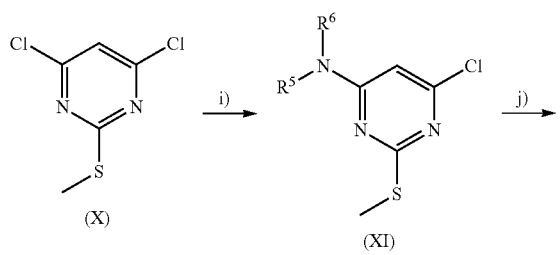

-continued

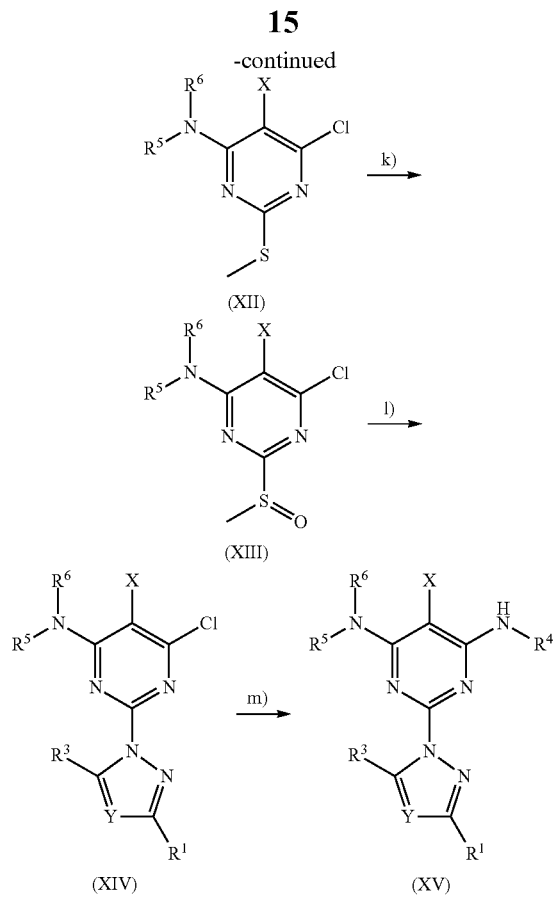

Reagents and conditions: Y = N or C—R²; (i) amine (6 eq), cesium carbonate, DMSO, 80° C.; (j) x = Cl, Br or I, N-chloro-, N-bromo- or N-iodosuccinimide (1.05 eq), DCM, RT; (k) m-chloroperbenzoic acid (1.1 eq), DCM, RT; (l) pyrazole or indazole derivative (1 eq), cesium carbonate, DMSO; (m) amine (6 eq), cesium carbonate, DMSO. 80° C.

Commercially available 4,6-dichloro-2-(methylthio)pyrimidine (Aldrich) is selectively substituted with primary, secondary amines, or optionally substituted pyrazole or triazole rings, by heating at temperatures between 60 and 80° C. in polar aprotic solvents such as acetonitrile or dimethylsulfoxide to yield the monosubstituted intermediate of formula (XI).

The introduction of a halogen atom in position 5 of the pyrimidine ring is performed by using the corresponding halo-succinimide derivatives and affords the compounds of formula (XII), according to the present invention. Subsequently oxidation of the thioether group of these derivatives of formula (XII) with meta-chlorperbenzoic acid yields the compounds of formula (XIII). These intermediates contain the methylsulfinyl group, which can be easily substituted in very mild reaction conditions by derivatives of optionally substituted pyrazole, triazole, indazole and azaindazole to afford compounds of formula (XIV). Finally the compounds of formula (XIV) are reacted at position 6 with a primary or secondary amine to form the compounds of formula (XV), which are the object of the present invention.

Pharmacological Activity

The "analysis of the activity of the enzyme Phosphodiesterase [³H] cAMP SPA" (Perkin Elmer #7090 TRKQ) kit was used for the study of Phosphodiesterase 10. The kit contains:

*Yttrium scintillation* proximity assay (SPA) in beads: yttrium silicate in microspheres resuspended pellet in MiliQ water containing 18 mM zinc sulfate.

10×PDE assay buffer: 500 mM Tris/HCl; 83 mM $MgCl_2$; 17 mM EGTA; pH 7.5.

Tracer [³H] cAMP: substrate for enzymatic reaction.

The test is based on the preferential binding of linear nucleotides to the SPA beads in the presence of zinc sulfate, with respect to the binding of cyclic nucleotides, which is almost imperceptible. Therefore, in optimum conditions, the product of the enzymatic reaction binds directly to SPA, and the substrate of the enzyme does not.

The binding of the radioactively labeled product to the beads brings the isotope to a proximity enough to allow the radioactive tritium radiation to excite the flashing part in the bead. Any independent radiolabel is not sufficiently close to the flashing part to allow the transfer of energy, so that no signal is generated. In addition, as the cyclic substrate is not effectively linked with the bead, the generated background signal is very low.

The binding of the linear nucleotides with the bead is based on a complex chelation mechanism. Zinc sulfate in the microsphere solution improves the binding between the bead and [³H]cAMP.

Phosphodiesterase 10A (PDE10A) Activity Inhibition Test

The test is performed in 96-well Flexiplates (Perkin Elmer #1450-401) with duplicates for each sample. Positive and negative controls are also required in each analyzed plate to evaluate the activity of the enzyme.

The inhibition values for each of the compounds are measured in duplicate at a concentration of 10 μM and the plate is incubated for 20 minutes at 30° C. and then 50 μL of the kit beads are then added "Phosphodiesterase SPA beads" (Perkin-Elmer #RPNQ0150).

The plate is stirred for 1 hour at room temperature. Then beads are allowed to stand for one hour before reading the activity in a beta scintillation counter.

TABLE 1

Test conditions

| | Sample | Positive control | Negative control |
|---|---|---|---|
| 10 x assay buffer | 10 μL | 10 μL | 10 μL |
| $H_2O$ | 60 μL | 60 μL | 70 μL |
| Compound | 10 μL | — | — |
| 1% DMSO | — | 10 μL | 10 μL |
| cAMP [³H] | 10 μL | 10 μL | 10 μL |
| PDE10A (0.002 U/μl) | 10 μL | 10 μL | — |

To build a dose-response curve, in order to calculate the potency of inhibition (expressed as $IC_{50}$) for PDE10A, a series of 1:10 dilutions in test in 1× buffer from 100 μM to 1 nM for each compound were carried out.

Results

Table 2 shows the decrease of the PDE10A activity ($IC_{50}$ values) of some of the compound of the present invention.

TABLE 2

| Compounds | Example | $IC_{50}$ PDE10 (nM) |
|---|---|---|
| 5-bromo-N⁴-(cyclopropylmethyl)-2-(1H-indazol-1-yl)pyrimidine-4,6-diamine | 1 | 52.5 |
| 5-bromo-N⁴-ethyl-2-(1H-indazol-1-yl)pyrimidine-4,6-diamine | 2 | 21.9 |
| 5-bromo-2-(1H-indazol-1-yl)-N⁴-(prop-2-ynyl)pyrimidine-4,6-diamine | 3 | 40.9 |
| 5-bromo-2-(1H-indazol-1-yl)-N⁴-[(2-methylthiazol-4-yl)methyl]pyrimidine-4,6-diamine | 6 | 18.8 |

TABLE 2-continued

| Compounds | Example | IC$_{50}$ PDE10 (nM) |
|---|---|---|
| 5-bromo-N$^4$-(tetrahydro-2H-pyran-4-yl)-2-(1H-indazol-1-yl)pyrimidine-4,6-diamine | 7 | 21.9 |
| 5-bromo-2-(1H-indazol-1-yl)-N$^4$-[(1-methyl-1H-pyrazol-4-yl)methyl]pyrimidine-4,6-diamine | 8 | 74.1 |
| 5-bromo-2-(1H-indazol-1-yl)-N$^4$-[(thiazol-5-yl)methyl]pyrimidine-4,6-diamine | 9 | 1.6 |
| 5-bromo-2-(1H-indazol-1-yl)-N$^4$-[(4-methylthiazol-5-yl)methyl]pyrimidine-4,6-diamine | 10 | 2.9 |
| 5-bromo-2-(1H-indazol-1-yl)-N$^4$-(2-methoxyethyl)pyrimidine-4,6-diamine | 11 | 25.9 |
| 5-bromo-N$^4$-(prop-2-ynyl)-2-[4-(pyridin-2-yl)-1H-pyrazol-1-yl]pyrimidine-4,6-diamine | 17 | 18 |
| 5-bromo-2-[4-(pyridin-2-yl)-1H-pyrazol-1-yl]-N$^4$-[(thiazol-5-yl)methyl]pyrimidine-4,6-diamine | 20 | 7 |
| 5-bromo-N$^4$-(tetrahydro-2H-pyran-4-yl)-2-[4-(quinolin-2-yl)-1H-pyrazol-1-yl]pyrimidine-4,6-diamine | 23 | 9.6 |
| 5-bromo-N$^4$-[(4-methylthiazol-5-yl)methyl]-2-[4-(pyrazin-2-yl)-1H-pyrazol-1-yl]pyrimidine-4,6-diamine | 29 | 16.5 |
| 5-bromo-N$^4$-(prop-2-ynyl)-2-[4-(pyrazin-2-yl)-1H-pyrazol-1-yl]pyrimidine-4,6-diamine | 30 | 4.5 |
| 5-bromo-N$^4$-(prop-2-ynyl)-2-(1H-pyrazolo[3,4-c]pyridin-1-yl)pyrimidine-4,6-diamine | 33 | 3.2 |
| 5-bromo-N$^4$-[(4-methylthiazol-5-yl)methyl]-2-(1H-pyrazolo[3,4-c]pyridin-1-yl)pyrimidine-4,6-diamine | 34 | 0.4 |
| 5-bromo-N$^4$-(cyclopropylmethyl)-2-(1H-pyrazolo[3,4-c]pyridin-1-yl)pyrimidine-4,6-diamine | 35 | 1.8 |
| 5-bromo-2-(1H-pyrazolo[3,4-c]pyridin-1-yl)-N$^4$-[(thiazol-5-yl)methyl]pyrimidine-4,6-diamine | 36 | 0.06 |
| 5-bromo-N$^4$-[(4-methylthiazol-5-yl)methyl]-2-(1H-pyrazolo[4,3-c]pyridin-1-yl)pyrimidine-4,6-diamine | 39 | 0.3 |
| 5-bromo-N$^4$-[(4-methylthiazol-5-yl)methyl]-2-(1H-pyrazolo[4,3-b]pyridin-1-yl)pyrimidine-4,6-diamine | 41 | 0.6 |
| 5-bromo-N$^4$-(prop-2-ynyl)-2-(1H-1,2,4-triazol-1-yl)pyrimidine-4,6-diamine | 42 | 5.8 |
| 5-bromo-N$^4$-[(thiazol-5-yl)methyl]-2-(1H-1,2,4-triazol-1-yl)pyrimidine-4,6-diamine | 45 | 1.3 |
| 5-bromo-N$^4$-(cyclopropylmethyl)-2-(1H-1,2,4-triazol-1-yl)pyrimidine-4,6-diamine | 46 | 3.4 |
| 1-[4-amino-5-bromo-6-(cyclopropylmethylamino)pyrimidin-2-yl]-1H-pyrazole-4-carboxylic acid | 51 | 29.9 |
| {1-[4-amino-5-bromo-6-(ethylamino)pyrimidin-2-yl]-1H-pyrazol-4-yl}(morpholino)methanone | 53 | 8.2 |
| 5-bromo-6-(1H-pyrazol-1-yl)-2-[4-(pyridin-2-yl)-1H-pyrazol-1-yl]pyrimidin-4-amine | 55 | 90.7 |
| 5-bromo-N$^4$-ethyl-2-[4-(pyrimidin-4-yl)-1H-pyrazol-1-yl]pyrimidine-4,6-diamine | 61 | 37.0 |
| 5-chloro-N$^4$-ethyl-2-(1H-indazol-1-yl)pyrimidine-4,6-diamine | 64 | 12.4 |
| 5-bromo-N$^4$-ethyl-2-(1H-indazol-1-yl)-N$^6$-(prop-2-ynyl)pyrimidine-4,6-diamine | 66 | 120 |
| N$^4$-[(1H-benzo[d]imidazol-2-yl)methyl]-5-bromo-N$^6$-ethyl-2-[4-(pyrimidin-4-yl)-1H-pyrazol-1-yl]pyrimidine-4,6-diamine | 77 | 29.3 |

The compounds of formula (I) have been tested according to the assay described above and have shown to be potent inhibitors of Phosphodiesterase 10.

Derivatives of the invention are useful in the treatment or prevention of diseases that are known to be improved by treatment with Phosphodiesterase 10 inhibitor.

Firstly, these diseases are related to cognitive disorders in central nervous system diseases, such as, for example, psychiatric diseases, such as schizophrenia or depression, or neurodegenerative diseases, such as Parkinson's disease, Huntington's disease and Alzheimer's disease.

Secondly, these diseases are related to respiratory disorders such as asthma, chronic obstructive pulmonary disease (COPD) and pulmonary hypertension.

Accordingly, another aspect of the invention relates to a compound of formula (I) as defined above, a pharmaceutically acceptable salt thereof, or a pharmaceutical composition comprising said compound of formula (I) and/or a pharmaceutically acceptable salt thereof, for use in medicine.

Another aspect relates to the use of a compound of formula (I) as defined above, a pharmaceutically acceptable salt thereof, or a pharmaceutical composition comprising said compound of formula (I) and/or a pharmaceutically acceptable salt thereof in medicine.

Another aspect relates to a method of treatment of diseases that are known to be improved by Phosphodiesterase 10 inhibitors, as defined above, comprising administering to a subject in need thereof an effective amount of a compound of formula (I) according to of the invention, pharmaceutically acceptable salts thereof, and/or pharmaceutical compositions comprising said compound and/or salts thereof. Preferably, the diseases that are known to be improved by Phosphodiesterase 10 inhibitors are selected from the group consisting of schizophrenia, depression, Parkinson's disease, Huntington's disease, Alzheimer's disease, pulmonary hypertension, asthma and COPD.

Another aspect relates to the use of a compound of formula (I) according to of the invention, pharmaceutically acceptable salts thereof, and/or pharmaceutical compositions comprising said compound and/or salts thereof, for the manufacture of a medicament for the treatment and/or prevention of diseases that are known to be improved by Phosphodiesterase 10 inhibitors, as defined above, preferably for the manufacture of a medicament for the treatment and/or prevention of a disease selected from the group consisting of schizophrenia, depression, Parkinson's disease, Huntington's disease, Alzheimer's disease, pulmonary hypertension, asthma and COPD.

Another aspect relates to the a compound of formula (I) according to of the invention, pharmaceutically acceptable salts thereof, and/or pharmaceutical compositions comprising said compound and/or salts thereof, for use in the treatment and/or prevention of diseases that are known to be improved by Phosphodiesterase 10 inhibitors, as defined above, preferably, for use in the treatment and/or prevention of a disease selected from the group consisting of schizophrenia, depression, Parkinson's disease, Huntington's disease, Alzheimer's disease, pulmonary hypertension, asthma and COPD.

The present invention also provides pharmaceutical compositions comprising, as active ingredient, at least one derivative of formula (I) or (II) or a pharmaceutically acceptable salt thereof, together with a pharmaceutically acceptable excipient, such as a vehicle or diluent. The active ingredient can understand 0.001% to 99% in weight, preferably from 0.01% to 90% in weight of the composition, depending on the nature of the formulation and if is a further dilution prior to application. Preferably, the compositions are prepared in a form suitable for oral, topical, nasal, rectal, percutaneous or injectable administration.

Pharmaceutically acceptable excipients that are mixed with the active compound, or salts of the compound, to form the compositions of this invention are well known per is and the particular excipients to be used depend inter alia of the intended procedure of administration of the compositions.

The compositions of this invention are adapted, preferably for injectable administration, pulmonary administration and per os. In this case, the compositions may take the form of tablets, long-acting tablets, sublingual tablets, capsules, aerosols for inhalation, solutions for inhalation, dry powder for inhalation or liquid preparations, such as mixtures, elixirs, syrups or suspensions, all of them comprising a compound according to the invention. These preparations can be prepared using procedures known in the art.

Diluents that can be used in the preparation of the compositions include liquid and solid diluents that are compatible with the active ingredient, along with coloring or flavoring agents, if desired. The tablets or capsules can contain, conveniently, between 2 and 500 mg of the active ingredient or the equivalent amount of a salt thereof.

The liquid composition adapted for oral use may be in the form of solutions or suspensions. Solutions can be aqueous solutions of a soluble salt or another derivative of the active compound together with, for example, sucrose to form a syrup. Suspensions can comprise an insoluble active compound of the invention or a pharmaceutically acceptable salt thereof together with water, and a suspending agent or flavoring agent.

Compositions for parenteral injection can be prepared from soluble salts, which can be dried or not by freezing and that can be dissolved in a pyrogen-free aqueous medium or another suitable fluid for parenteral injection.

The effective doses are normally in the range of 2-2000 mg of active ingredient per day. Daily dosage can be administered in one or more treatments, preferably 1 to 4 treatments per day.

The present invention is further illustrated by the following examples. Examples are for illustrative purposes only and are not intended to be limiting.

The synthesis of the compounds of the invention and intermediates used therein are illustrated by the following examples (1 to 78), including the preparation of intermediates, which does not limit in any way the scope of the present invention.

EXAMPLES

General. Reagents, solvents and starting products were acquired from commercial sources. The term "concentration" refers to the vacuum evaporation using a Büchi rotavapor. When indicated, the reaction products were purified by "flash" chromatography on silica gel (40-63 μm) with the indicated solvent system. The spectroscopic data were measured in aVarian Mercury 400 spectrometer. The melting points were measured in a Büchi 535 instrument. The HPLC-MS were performed on a Gilson instrument equipped with a Gilson 321 piston pump, a Gilson 864 vacuum degasser, a Gilson 189 injection module, a 1/1000 Gilson splitter, a Gilson 307 pump, a Gilson 170 detector, and a Thermoquest Fennigan aQa detector.

Intermediate 1:
5-bromo-6-chloro-2-(methylthio)pyrimidine-4-amine

To a cold stirring solution of 10 g (52.2 mmol) 6-chloro-2-(methylsulfinyl)pyrimidine-4-amine in 450 ml of DCM, 10 g (56.2 mmol) of N-bromosuccinimide were added, and stirring was continued for 1 hour at room temperature to provide 5-bromo-6-chloro-2-(methylthio)pyrimidine-4-amine, which was used without further purification in the next step (see intermediate 3). The end of the reaction is followed by thin layer chromatography.

The following intermediate was synthesized using the procedure described for intermediate 1, but using N-chlorosuccinimide.

Intermediate 2:
5,6-dichloro-2-(methylthio)pyrimidine-4-amine $^1$H-NMR (400 MHz, DMSO-$d_6$): δ=2.40 (s, 3H), 7.46 (s, 1H), 7.98 (s, 1H).

Intermediate 3: 5-bromo-6-chloro-2-(methylsulfinyl)pyrimidine-4-amine

To a stirring solution of 5-bromo-6-chloro-2-(methylthio)pyrimidine-4-amine (intermediate 1) (52.2 mmol) in 450 ml of DCM, a solution of 12.9 g (57.4 mmol) of m-chloroperbenzoic acid (77%) (Sigma-Aldrich) in 100 ml of DCM was slowly added. The reaction mixture was stirred at room temperature for 1 hour. The formed white precipitate was filtered, washed several times with DCM and dried. 13.96 g of 5-bromo-6-chloro-2-(methylsulfinyl)pyrimidine-4-amine were obtained (98.9%).

$^1$H-NMR (400 MHz, DMSO-$d_6$): δ=2.78 (s, 3H), 8.17 (d, 2H).

HPLC-MS: Rt 2.058 m/z 270.8 (MH$^+$).

The following intermediate was synthesized using the procedure described for intermediate 3, but starting from intermediate 2.

Intermediate 4:
5,6-dichloro-2-(methylsulfinyl)pyrimidine-4-amine $^1$H-NMR (400 MHz, DMSO-$d_6$): δ=2.79 (s, 3H), 8.58 (s, 2H).

Intermediate 5: 5-bromo-6-chloro-2-(1H-indazol-1-yl)pyrimidine-4-amine

To a vigorously stirring suspension of 2 g (7.4 mmol) of 5-bromo-6-chloro-2-(methylsulfinyl)pyrimidine-4-amine (intermediate 3) in 40 ml of DMF, 0.87 g (7.4 mmol) indazole and 1.4 g (4.4 mmol) of cesium carbonate were added. The reaction mixture was stirred at room temperature for 20 minutes. The solution was poured onto 200 ml of ice-water. The resulting precipitate was filtered, washed with cold water and dried. The desired product is obtained as a white solid 1.31 g (54.6%)

$^1$H-NMR (400 MHz, DMSO-$d_6$): δ=7.34 (t, 1H), 7.46 (s, 1H), 7.56 (t, 1H), 7.87 (d, 1H), 8.41 (s, 1H), 8.46 (s, 1H), 8.71 (d, 1H).

HPLC-MS: Rt 4.228 m/z 325.0 (MH$^+$).

The following intermediates were synthesized using the procedure described for intermediate 5, but starting from the corresponding pyrazoles.

Intermediate 6: 5-Bromo-6-chloro-2-(1H-pyrazol-1-yl)pyrimidine-4-amine $^1$H-NMR (400 MHz, DMSO-$d_6$): δ=6.56 (t, 1H), 7.81 (d, 1H), 8.44 (d, 1H), 8.15 (d, 2H).

HPLC-MS: RRt 3.113 m/z 307.9 (MH$^+$).

Intermediate 7: 5-bromo-6-chloro-2-[4-(pyridin-4-yl)-1H-pyrazol-1-yl]pyrimidine-4-amine $^1$H-NMR (400 MHz, DMSO-d$_6$): δ=7.58 (s, 1H), 7.78 (d, 2H), 8.43 (s, 1H), 8.47 (s, 1H), 8.58 (d, 2H), 9.12 (s, 1H).

Intermediate 8: 5-bromo-6-chloro-2-[4-(pyridin-2-yl)-1H-pyrazol-1-yl]pyrimidine-4-amine $^1$H-NMR (400 MHz, DMSO-d$_6$): δ=7.25 (t, 1H), 7.57 (s, 1H), 7.84 (m, 2H), 8.37 (s, 1H), 8.42 (s, 1H), 8.56 (d, 1H), 8.96 (s, 1H).
HPLC-MS: Rt 3,360 m/z 351.9 (MH$^+$).

Intermediate 9: 5-bromo-6-chloro-2-[4-(quinolin-2-yl)-1H-pyrazol-1-yl]pyrimidin-4-amine $^1$H-NMR (400 MHz, DMSO-d$_6$): δ=7.56 (m, 2H), 7.75 (t, 1H), 7.95 (d, 1H), 7.99 (d, 1H), 8.05 (d, 1H), 8.39 (d, 1H), 8.49 (s, 2H), 8.54 (s, 1H), 9.15 (s, 1H).
HPLC-MS: Rt 4.172 m/z 401.9 (MH$^+$).

Intermediate 10: 5-bromo-6-chloro-2-(4-phenyl-1H-pyrazol-1-yl)pyrimidine-4-amine $^1$H-NMR (400 MHz, DMSO-d$_6$): δ=7.26 (t, 1H), 7.40 (t, 2H), 7.56 (s, 1H), 7.70 (d, 2H), 8.18 (s, 1H), 8.82 (s, 1H).
HPLC-MS: Rt 4,250 m/z 351.0 (MH$^+$).

Intermediate 11: 5-bromo-6-chloro-2-[4-(4-chlorophenyl)-1H-pyrazol-1-yl]pyrimidine-4-amine $^1$H-NMR (400 MHz, DMSO-d$_6$): δ=7.44 (d, 2H), 7.52 (s, 1H), 7.78 (d, 2H), 8.31 (s, 1H), 8.42 (s, 1H), 8.86 (s, 1H).
HPLC-MS: Rt 4.646 m/z 385.9 (MH$^+$).

Intermediate 12: 5-bromo-6-chloro-2-[4-(pyrazin-2-yl)-1H-pyrazol-1-yl]pyrimidin-4-amine $^1$H-NMR (400 MHz, DMSO-d$_6$): δ=7.58 (s, 2H), 8.45 (s, 1H), 8.50 (d, 1H), 8.62 (s, 1H), 9.10 (s, 1H), 9.18 (d, 1H).
HPLC-MS: Rt 3.057 m/z 353.0 (MH$^+$).

Intermediate 13: 5-bromo-6-chloro-2-(1H-pyrazolo[3,4-b]pyridin-1-yl)pyrimidine-4-amine $^1$H-NMR (400 MHz, DMSO-d$_6$): δ=7.17 (t, 1H), 7.69 (s, 1H), 8.28 (d, 1H) 8.64 (s, 1H), 8.72 (s, 1H), 9.11 (d, 1H).
HPLC-MS: Rt 3,003 m/z 325.9 (MH$^+$).

Intermediate 14: 5-bromo-6-chloro-2-(1H-pyrazolo[3,4-c]pyridin-1-yl)pyrimidine-4-amine $^1$H-NMR (400 MHz, DMSO-d$_6$): δ=7.58 (s, 1H), 7.88 (d, 1H), 8.47 (d, 1H), 8.54 (s, 1H), 8.56 (s, 1H), 10.08 (d, 1H).
HPLC-MS: Rt 2.971 m/z 326.0 (MH$^+$).

Intermediate 15: 5-bromo-6-chloro-2-(1H-pyrazolo[4,3-c]pyridin-1-yl)pyrimidine-4-amine $^1$H-NMR (400 MHz, DMSO-d$_6$): δ=7.57 (s, 1H), 8.58 (d, 1H), 8.60 (s, 1H), 9.19 (s, 1H).
HPLC-MS: Rt 2.973 m/z 326.0 (MH$^+$).

Intermediate 16: 5-bromo-6-chloro-2-(1H-pyrazolo[4,3-b]pyridin-1-yl)pyrimidine-4-amine $^1$H-NMR (400 MHz, DMSO-d$_6$): δ=7.56 (m, 2H), 8.51 (s, 1H), 8.62 (s, 1H), 8.67 (d, 1H), 9.02 (d, 1H).
HPLC-MS: Rt 3.179 m/z 326.0 (MH$^+$).

Intermediate 17: 5-bromo-6-chloro-2-(1H-1,2,4-triazol-1-yl)pyrimidine-4-amine $^1$H-NMR (400 MHz, DMSO-d$_6$): δ=7.66 (s, 1H), 8.24 (s, 1H), 8.57 (s, 1H), 9.17 (s, 1H).
HPLC-MS: Rt 2.410 m/z 276.9 (MH$^+$).

Intermediate 18: ethyl 1-(4-amino-5-bromo-6-chloropyrimidin-2-yl)-1H-pyrazol-4-carboxylate $^1$H-NMR (400 MHz, DMSO-d$_6$): δ=1.28 (t, 3H), 4.25 (c, 2H), 7.63 (s, 1H), 8.14 (s, 1H) 8.49 (s, 1H), 8.79 (s, 1H).
HPLC-MS: Rt 3.638 m/z 347.9 (MH$^+$).

Intermediate 19: N$^4$-ethyl-2-(methylthio)pyrimidine-4,6-diamine

A mixture of 1.00 g (5.69 mmol) of 6-chloro-2-(methylthio)pyrimidine-4-amine and 4.5 ml (57 mmol) of ethylamine (70% in water) in 3 ml of DMSO was stirred for 48 hours at 65° C. in a closed glass tube. The solution was poured onto 20 ml of cold water. The formed precipitate was filtered, washed several times with cold water and dried. 0.79 g (75.3%) of a white solid were obtained.

$^1$H-NMR (400 MHz, DMSO-d$_6$): δ=1.06 (t, 3H), 2.31 (s, 3H), 3.13 (m, 2H), 5.07 (s, 1H), 6.03 (s, 2H), 6.52 (t, 1H).
HPLC-MS: Rt 2.355 m/z 185.0 (MH$^+$).

The following intermediate was synthesized using the procedure described for intermediate 19, but using 1H-pyrazole.

Intermediate 20: 2-(methylthio)-6-(1H-pyrazol-1-yl)pyrimidine-4-amine

HPLC-MS: Rt 3.136 m/z 208.0 (MH$^+$).

Intermediate 21: 5-bromo-N$^4$-ethyl-2-(methylthio)pyrimidine-4,6-diamine

To a stirring solution of 0.774 g (4.2 mmol) of N$^4$-ethyl-2-(methylthio)pyrimidine-4,6-diamine (intermediate 19) in 10 ml of DCM, 0.75 g (4.2 mmol) of N-bromosuccinimide were added, and stirring was continued for 4 hours at room temperature to generate 5-bromo-N$^4$-ethyl-2-(methylthio) pyrimidine-4,6-diamine, which was used without further purification in the next step (see intermediate 24). The completion of the reaction is monitored by thin layer chromatography.

$^1$H-NMR (400 MHz, DMSO-d$_6$): δ=1.08 (t, 3H), 2.35 (s, 3H), 3.33 (m, 2H), 6.38 (s, 2H), 6.50 (t, 1H).
HPLC-MS: Rt 3.668 m/z 263.9 (MH$^+$).

The following intermediate was synthesized using the procedure described for intermediate 21.

Intermediate 22: 5-bromo-2-(methylthio)-6-(1H-pyrazol-1-yl)pyrimidine-4-amine This intermediate was used without further purification in the next step (see intermediate 25).

The following intermediate was synthesized using the procedure described for intermediate 21, but with N-chlorosuccinimide.

Intermediate 23: 5-chloro-$N^4$-ethyl-2-(methylthio)pyrimidine-4,6-diamine

This intermediate was used without further purification in the next step (see intermediate 26).

Intermediate 24: 5-bromo-$N^4$-ethyl-2-(methylsulfinyl)pyrimidine-4,6-diamine To a stirring solution of 5-bromo-$N^4$-ethyl-2-(methylthio)pyrimidine-4,6-diamine (intermediate 19) (4.2 mmol) in 10 ml of DCM, 1.04 g (4.6 mmol) of m-chloroperbenzoic acid (77%) (Aldrich) in 3 ml of DCM were added dropwise. The reaction mixture was stirred at room temperature for 1 hour. After evaporation of the solvent under reduced pressure, the remaining solid was first washed with cold DCM and then several times with cold water, filtered and dried. 1.11 g (95%) of 5-bromo-$N^4$-ethyl-2-(methylsulfinyl)pyrimidine-4,6-diamine were obtained.
$^1$H-NMR (400 MHz, DMSO-$d_6$): δ=1.08 (t, 3H), 2.72 (s, 3H), 3.36 (m, 2H), 6.90 (m, 3H).
HPLC-MS: Rt 2.172 m/z 280.9 (MH$^+$).

The following intermediates were synthesized using the procedure described for intermediate 24.

Intermediate 25: 5-bromo-2-(methylsulfinyl)-6-(1H-pyrazol-1-yl)pyrimidine-4-amine HPLC-MS: Rt 1.906 m/z 303.9 (MH$^+$).

Intermediate 26: 5-chloro-$N^4$-ethyl-2-(methylsulfinyl)pyrimidine-4,6-diamine $^1$H-NMR (400 MHz, DMSO-$d_6$): δ=1.08 (t, 3H), 2.72 (s, 3H), 3.34 (m, 2H), 6.93 (s, 2H), 7.05 (t, 1H).
HPLC-MS: Rt 2.079 m/z 235.0 (MH$^+$).

Intermediate 27: 6-chloro-2-(methylthio)-N-(prop-2-ynyl)pyrimidine-4-amine

A mixture of 1.00 g (5.13 mmol) of 4,6-dichloro-2-(methylthio)pyrimidine and 0.7 ml (10.3 mmol) of propargylamine in 10 ml of acetonitrile was stirred for 12 hours at 60° C. The reaction solution was poured onto cold water. Then, the formed precipitate was filtered, washed several times with cold water and dried. 1.09 g of a light yellow solid were obtained.
$^1$H-NMR (400 MHz, DMSO-$d_6$): δ=2.43 (s, 3H), 3.16 (s, 1H), 4.11 (d, 2H), 6.26 (s, 1H), 8.14 (t, 1H).
HPLC-MS: Rt 3.815 m/z 213.9 (MH$^+$).

The following intermediate was synthesized using the procedure described for intermediate 27, but starting from the corresponding amide.

Intermediate 28: 6-chloro-N-ethyl-2-(methylthio)pyrimidine-4-amine $^1$H-NMR (400 MHz, DMSO-$d_6$): δ=1.09 (t, 3H), 2.40 (s, 3H), 3.31 (m, 2H), 6.16 (s, 1H), 7.74 (t, 1H).
HPLC-MS: Rt 3.912 m/z 204.0 (MH$^+$).

Intermediate 29: 5-bromo-6-chloro-2-(methylthio)-N-(prop-2-ynyl)pyrimidine-4-amine To a stirring solution of 1.16 g (5.45 mmol) of 6-chloro-2-(methylthio)-N-(prop-2-ynyl)pyrimidine-4-amine (intermediate 27) in 6 ml of DCM, 1.07 g (6.0 mmol) of N-bromosuccinimide were added, and stirring was continued for 4 hours at room temperature to give 5-bromo-6-chloro-2-(methylthio)-N-(prop-2-ynyl)pyrimidine-4-amine, which was used without further purification in the next step (see intermediate 31). The completion of the reaction is monitored by thin layer chromatography.

The following intermediate was synthesized using the procedure described for intermediate 29.

Intermediate 30: 5-bromo-6-chloro-N-ethyl-2-(methylthio)pyrimidine-4-amine

This intermediate was used without further purification in the next step (see intermediate 32).

Intermediate 31: 5-bromo-6-chloro-2-(methylsulfinyl)-N-(prop-2-ynyl)pyrimidine-4-amine To a stirring solution of 5-bromo-6-chloro-2-(methylthio)-N-(prop-2-ynyl)pyrimidine-4-amine (intermediate 29) (5.45 mmol) in 6 ml of DCM, 1.34 g (6 mmol) of m-chloroperbenzoic acid (77%) (Aldrich) in 8 ml of DCM were added dropwise. The reaction mixture was stirred at room temperature for 1 hour. The precipitate was filtered, washed several times with cold DCM and dried. 1.52 g (90.5%) of 5-bromo-6-chloro-2-(methylsulfinyl)-N-(prop-2-ynyl)pyrimidine-4-amine were obtained as a light brown solid.
HPLC-MS: Rt 2.506 m/z 308.9 (MH$^+$).

The following intermediate was synthesized using the procedure described for intermediate 31.

Intermediate 32: 5-bromo-6-chloro-N-ethyl-2-(methylsulfinyl)pyrimidine-4-amine HPLC-MS: Rt 2.605 m/z 299.9 (MH$^+$).

Intermediate 33: 5-bromo-6-chloro-2-(1H-indazol-1-yl)-N-(prop-2-ynyl)pyrimidine-4-amine To a suspension of 0.5 g (1.62 mmol) of 5-bromo-6-chloro-2-(methylsulfinyl)-N-(prop-2-ynyl)pyrimidine-4-amine (intermediate 31) in 2 ml of DMSO, 0.19 g (1.62 mmol) indazole and 0.32 g of cesium carbonate were added. The slightly yellow solution was stirred at room temperature for 20 minutes. The reaction mixture was poured onto 10 ml of cold water. The resulting precipitate was filtered, washed with cold water and dried. The desired product was obtained as a white solid 0.31 g (52.8%).
$^1$H-NMR (400 MHz, DMSO-$d_6$): δ=3.11 (s, 1H), 4.23 (d, 2H), 7.27 (t, 1H), 7.38 (t, 1H), 7.56 (t, 1H), 7.89 (d, 1H), 8.38 (s, 1H), 8.93 (d, 1H).

The following intermediates were synthesized using the procedure described for intermediate 33.

Intermediate 34: 5-bromo-6-chloro-N-(prop-2-ynyl)-2-[4-(pyridin-2-yl)-1H-pyrazol-1-yl]pyrimidine-4-amine $^1$H-NMR (400 MHz, DMSO-$d_6$): δ=3.09 (s, 1H), 4.23 (d, 2H), 7.27 (t, 1H), 7.29 (t, 1H), 7.84 (s, 1H), 7.88 (s, 1H), 8.32 (s, 1H), 8.65 (d, 1H), 9.11 (s, 1H).

Intermediate 35: 5-bromo-6-chloro-N-ethyl-2-[4-(pyrimidin-4-yl)-1H-pyrazol-1-yl]pyrimidine-4-amine HPLC-MS: Rt 3.605 m/z 381.0 (MH⁺).

EXAMPLES

Derivatives of Intermediate 5

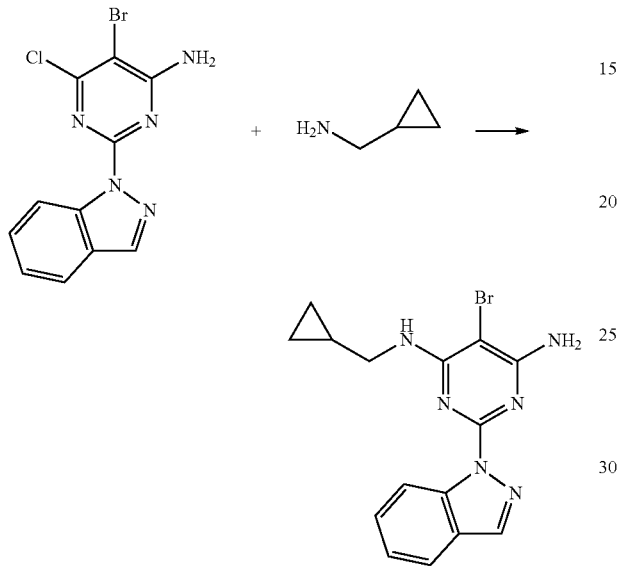

Example 1

5-bromo-$N^4$-(cyclopropylmethyl)-2-(1H-indazol-1-yl)pyrimidine-4,6-diamine

A mixture of 0.1 g (0.31 mmol) of 5-bromo-6-chloro-2-(1H-indazol-1-yl)pyrimidine-4-amine (intermediate 5) and 160 μl (1.85 mmol) of cyclopropylmethylamine in 0.5 ml of DMSO in a closed glass tube was stirred for 5 h at 65° C. The reaction mixture was poured onto 20 ml of cold water. The formed white precipitate was filtered, washed several times with water and dried. 0.088 g (79.7%) of the desired compound were obtained.

HPLC-MS: Rt 4.521 m/z 361.0 (MH⁺).
$^1$H-NMR (400 MHz, DMSO-$d_6$): δ=0.31 (m, 2H), 0.41 (m, 2H), 1.17 (m, 1H) 3.34 (m, 2H), 6.77 (s, 2H), 7.27 (m, 2H), 7.49 (t, 1H), 7.83 (d, 1H), 8.31 (s, 1H), 8.72 (d, 1H).

Compounds of examples of 2 to 11 were synthesized using the procedure described for example 1 from 5-bromo-6-chloro-2-(1H-indazol-1-yl)pyrimidine-4-amine (intermediate 5) and the corresponding amines or pyrazoles:

Example 2

5-bromo-$N^4$-ethyl-2-(1H-indazol-1-yl)pyrimidine-4,6-diamine

HPLC-MS: Rt 4.077 m/z 335.0 (MH⁺).
$^1$H-NMR (400 MHz, DMSO-$d_6$): δ=1.20 (t, 3H), 3.51 (m, 2H) 6.75 (s, 2H), 6.88 (t, 1H), 7.27 (m, 1H), 7.50 (m, 1H) 7.83 (d, 1H), 8.31 (s, 1H) 8.70 (d, 1H).

Example 3

5-bromo-2-(1H-indazol-1-yl)-$N^4$-(prop-2-ynyl)pyrimidine-4,6-diamine

HPLC-MS: Rt 3.765 m/z 345.0 (MH⁺).
$^1$H-NMR (400 MHz, DMSO-$d_6$): δ=3.09 (s, 1H), 4.21 (d, 2H), 6.88 (s, 2H), 7.18 (t, 1H), 7.28 (t, 1H), 7.48 (t, 1H), 7.83 (d, 1H), 8.32 (s, 1H), 8.83 (d, 1H).

Example 4

5-bromo-2-(1H-indazol-1-yl)-6-(1H-pyrazol-1-yl)pyrimidine-4-amine

HPLC-MS: Rt 3.679 m/z 356.0 (MH⁺).
$^1$H-NMR (400 MHz, DMSO-$d_6$): δ=6.61 (s, 1H), 7.34 (t, 1H), 7.51 (s, 1H), 7.56 (t, 1H), 7.88 (m, 2H), 8.42 (m, 3H), 8.73 (d, 1H).

Example 5

$N^4$-[(1H-benzo[d]imidazol-2-yl)methyl]-5-bromo-2-(1H-indazol-1-yl)pyrimidine-4,6-diamine HPLC-MS: Rt 3.962 m/z 435.0 (MH⁺).

Example 6

5-bromo-2-(1H-indazol-1-yl)-$N^4$-[(2-methylthiazol-4-yl)methyl]pyrimidine-4,6-diamine HPLC-MS: Rt 3.744 m/z 416.0 (MH⁺).
$^1$H-NMR (400 MHz, DMSO-$d_6$): δ=2.65 (s, 3H), 4.71 (d, 2H), 6.83 (s, 2H), 7.19 (s, 1H), 7.23 (t, 1H), 7.27 (t, 1H), 7.34 (t, 1H), 7.79 (d, 1H), 8.29 (s, 1H), 8.37 (d, 1H).

Example 7

5-bromo-$N^4$-(tetrahydro-2H-pyran-4-yl)-2-(1H-indazol-1-yl)pyrimidine-4,6-diamine HPLC-MS: Rt 3.714 m/z 389.0 (MH⁺).
$^1$H-NMR (400 MHz, DMSO-$d_6$): δ=1.72 (m, 2H), 1.85 (m, 2H), 3.43 (m, 2H), 3.91 (m, 2H), 4.25 (m, 1H), 6.35 (t, 1H), 6.81 (s, 2H), 7.28 (m, 1H), 7.51 (m, 1H), 7.84 (d, 1H), 8.32 (s, 1H), 8.66 (d, 1H).

Example 8

5-bromo-2-(1H-indazol-1-yl)-$N^4$-[(1-methyl-1H-pyrazol-4-yl)methyl]pyrimidine-4,6-diamine HPLC-MS: Rt 3.321 m/z 401.0 (MH⁺).
$^1$H-NMR (400 MHz, DMSO-$d_6$): δ=3.72 (s, 3H), 4.47 (d, 2H), 6.77 (s, 2H), 7.06 (s, 1H), 7.28 (t, 1H), 7.44 (s, 1H), 7.46 (t, 1H), 7.66 (1H), 7.83 (d, 1H), 8.34 (s, 1H), 8.66 (d, 1H).

Example 9

5-bromo-2-(1H-indazol-1-yl)-$N^4$-[(thiazol-5-yl)methyl]pyrimidine-4,6-diamine

HPLC-MS: Rt 3.270 m/z 402.0 (MH⁺).

¹H-NMR (400 MHz, DMSO-d₆): δ=4.86 (d, 2H), 6.88 (s, 2H), 7.08 (t, 1H), 7.28 (t, 1H), 7.47 (t, 1H), 7.83 (d, 1H), 7.88 (d, 1H), 8.34 (s, 1H), 8.62 (d, 1H), 8.88 (s, 1H).

Example 10

5-bromo-2-(1H-indazol-1-yl)-N⁴-[(4-methylthiazol-5-yl)methyl]pyrimidine-4,6-diamine HPLC-MS: Rt 3.402 m/z 416.0 (MH⁺).
¹H-NMR (400 MHz, DMSO-d₆): δ=2.45 (s, 3H), 4.78 (d, 2H), 6.87 (s, 2H), 7.07 (t, 1H), 7.26 (t, 1H), 7.49 (t, 1H), 7.82 (d, 1H), 8.31 (s, 1H), 8.51 (d, 1H), 8.72 (s, 1H).

Example 11

5-bromo-2-(1H-indazol-1-yl)-N⁴-(2-methoxyethyl)pyrimidine-4,6-diamine

HPLC-MS: Rt 3.633 m/z 365.0 (MH⁺).
¹H-NMR (400 MHz, DMSO-d₆): δ=3.28 (s, 3H), 3.54 (t, 2H), 3.64 (m, 2H), 6.62 (t, 1H), 6.79 (s, 2H), 7.27 (t, 1H), 7.48 (t, 1H), 7.84 (d, 1H), 8.31 (s, 1H), 8.68 (d, 1H).
Compounds of examples from 12 to 46 were synthesized using the procedure described for example 1 from the corresponding intermediate and amines or pyrazoles:

Derivatives of Intermediate 6

Example 12

5-bromo-N⁴-[(4-methylthiazol-5-yl)methyl]-2-(1H-pyrazol-1-yl)pyrimidine-4,6-diamine ¹H-NMR (400 MHz, DMSO-d₆): δ=2.44 (s, 3H), 4.71 (d, 2H), 6.48 (t, 1H), 6.52 (t, 1H), 6.84 (s, 2H), 7.48 (t, 1H), 7.70 (d, 1H), 8.49 (d, 1H), 8.74 (s, 1H).
HPLC-MS: Rt 2.919 m/z 366.0 (MH⁺).

Example 13

5-bromo-N⁴-(2-methoxyethyl)-2-(1H-pyrazol-1-yl)pyrimidine-4,6-diamine

¹H-NMR (400 MHz, DMSO-d₆): δ=3.30 (s, 3H), 3.48 (t, 2H), 3.57 (m, 2H), 6.46 (t, 1H), 6.61 (t, 1H), 6.76 (s, 2H), 7.69 (d, 1H), 8.43 (d, 1H).
HPLC-MS: Rt 2.787 m/z 315.0 (MH⁺).

Example 14

N⁴-[(1H-benzo[d]imidazol-2-yl)methyl]-5-bromo-2-(1H-pyrazol-1-yl)pyrimidine-4,6-diamine ¹H-NMR (400 MHz, DMSO-d₆): δ=4.75 (d, 2H), 6.47 (t, 1H), 6.90 (s, 1H), 7.11 (m, 2H), 7.47 (m, 2H), 7.60 (s, 1H), 7.80 (s, 1H), 8.37 (d, 1H).

Derivatives of Intermediate 7

Example 15

5-bromo-N⁴-(prop-2-ynyl)-2-[4-(pyridin-4-yl)-1H-pyrazol-1-yl]pyrimidine-4,6-diamine ¹H-NMR (400 MHz, DMSO-d₆): δ=3.06 (s, 1H), 4.22 (d, 2H), 6.90 (s, 2H), 7.19 (t, 1H), 7.79 (d, 1H), 8.47 (s, 1H), 8.59 (d, 2H), 9.16 (s, 1H).
HPLC-MS: Rt 3.343 m/z 370.0 (MH⁺).

Example 16

5-bromo-2-[4-(pyridin-4-yl)-1H-pyrazol-1-yl]-N⁴-[(thiazol-5-yl)methyl]pyrimidine-4,6-diamine ¹H-NMR (400 MHz, DMSO-d₆): δ=4.85 (d, 2H), 6.92 (s, 2H), 7.56 (t, 1H), 7.80 (d, 2H), 7.88 (s, 1H), 8.33 (s, 1H), 8.60 (d, 2H), 8.88 (s, 1H), 9.21 (s, 1H).
HPLC-MS: Rt 3.124 m/z 429.0 (MH⁺).

Derivatives of Intermediate 8

Example 17

5-bromo-N⁴-(prop-2-ynyl)-2-[4-(pyridin-2-yl)-1H-pyrazol-1-yl]pyrimidine-4,6-diamine ¹H-NMR (400 MHz, DMSO-d₆): δ=3.06 (s, 1H), 4.22 (d, 2H), 6.90 (s, 2H), 7.19 (t, 1H), 7.24 (t, 1H), 7.80 (s, 1H), 7.81 (s, 1H), 8.29 (s, 1H), 8.57 (d, 1H), 9.03 (s, 1H).
HPLC-MS: Rt 3.236 m/z 370.0 (MH⁺).

Example 18

5-bromo-N⁴-(cyclopropylmethyl)-2-[4-(pyridin-2-yl)-1H-pyrazol-1-yl]pyrimidine-4,6-diamine ¹H-NMR (400 MHz, DMSO-d₆): δ=0.31 (m, 2H), 0.42 (m, 2H), 1.14 (m, 1H), 3.32 (t, 2H), 6.78 (s, 2H), 6.82 (t, 1H), 7.24 (t, 1H), 7.80 (s, 1H), 7.81 (s, 1H), 8.28 (s, 1H), 8.56 (d, 1H), 8.95 (s, 1H).
HPLC-MS: Rt 3.870 m/z 386.0 (MH⁺).

Example 19

5-bromo-N⁴-[(4-methylthiazol-5-yl)methyl]-2-(4-(pyridin-2-yl)-1H-pyrazol-1-yl)pyrimidine-4,6-diamine ¹H-NMR (400 MHz, DMSO-d₆): δ=2.46 (s, 3H), 4.77 (d, 2H), 6.91 (s, 2H), 7.26 (t, 1H), 7.53 (t, 1H), 7.81 (s, 1H), 7.88 (s, 1H), 8.30 (s, 1H), 8.56 (d, 1H), 8.76 (s, 1H), 8.90 (s, 1H).
HPLC-MS: Rt 3.157 m/z 445.0 (MH⁺).

Example 20

5-bromo-2-[4-(pyridin-2-yl)-1H-pyrazol-1-yl]-N⁴-[(thiazol-5-yl)methyl]pyrimidine-4,6-diamine ¹H-NMR (400 MHz, DMSO-d₆): δ=4.85 (d, 2H), 6.91 (s, 2H), 7.24 (t, 1H), 7.53 (t, 1H), 7.81 (s, 2H), 7.88 (s, 1H), 8.31 (s, 1H), 8.55 (d, 1H), 8.88 (s, 1H), 9.11 (s, 1H).
HPLC-MS: Rt 3.056 m/z 429.0 (MH⁺).

Example 21

5-bromo-N⁴-(2-methoxyethyl)-2-[4-(pyridin-2-yl)-1H-pyrazol-1-yl]pyrimidine-4,6-diamine ¹H-NMR (400 MHz, DMSO-d₆): δ=3.28 (s, 3H), 3.51 (t, 2H), 3.62 (m, 2H), 6.64 (t, 1H), 6.81 (s, 2H), 7.24 (t, 1H), 7.80 (s, 2H), 8.28 (s, 1H), 8.56 (d, 1H), 8.97 (s, 1H).
HPLC-MS: Rt 3.212 m/z 391.0 (MH⁺).

Derivatives of Intermediate 9

Example 22

5-bromo-N[4]-(prop-2-ynyl)-2-[4-(quinolin-2-yl)-1H-pyrazol-1-yl]pyrimidine-4,6-diamine HPLC-MS: Rt 3.903 m/z 420.0 (MH$^+$).
$^1$H-NMR (400 MHz, DMSO-$d_6$): δ=3.08 (s, 1H), 4.27 (d, 2H), 6.94 (s, 2H), 7.21 (t, 1H), 7.55 (t, 1H), 7.74 (t, 1H), 7.94 (d, 1H), 7.98 (d, 1H), 8.02 (d, 1H), 8.38 (d, 1H), 8.46 (s, 1H), 9.22 (s, 1H).

Example 23

5-bromo-N[4]-(tetrahydro-2H-pyran-4-yl)-2-[4-(quinolin-2-yl)-1H-pyrazol-1-yl]pyrimidine-4,6-diamine HPLC-MS: Rt 3.863 m/z 468.1 (MH$^+$).
$^1$H-NMR (400 MHz, DMSO-$d_6$): δ=1.69 (m, 2H), 1.82 (m, 2H), 3.47 (m, 2H), 3.90 (m, 2H), 4.30 (m, 1H), 6.39 (d, 1H), 6.85 (s, 2H), 7.55 (t, 1H), 7.75 (t, 1H), 7.94 (d, 1H), 7.98 (d, 1H), 8.02 (d, 1H), 8.39 (d, 1H), 8.45 (s, 1H), 9.13 (s, 1H).

Example 24

5-bromo-N[4]-[(2-methylthiazol-4-yl)methyl]-2-[4-(quinolin-2-yl)-1H-pyrazol-1-yl]pyrimidine-4,6-diamine HPLC-MS: Rt 4,025 m/z 493.0 (MH$^+$).
$^1$H-NMR (400 MHz, DMSO-$d_6$): δ=2.69 (s, 3H), 4.73 (d, 2H), 6.87 (s, 2H), 7.39 (s, 1H), 7.63 (m, 1H), 7.72 (t, 1H), 8.00 (d, 1H), 8.33 (s, 1H), 8.36 (d, 1H), 8.44 (d, 1H), 8.49 (d, 1H), 9.06 (s, 1H), 9.09 (s, 1H).

Example 25

5-bromo-N[4]-[(4-methylthiazol-5-yl)methyl]-2-[4-(quinolin-2-yl)-1H-pyrazol-1-yl]pyrimidine-4,6-diamine HPLC-MS: Rt 3.810 m/z 493.0 (MH$^+$).
$^1$H-NMR (400 MHz, DMSO-$d_6$): δ=2.51 (s, 3H), 4.80 (d, 2H), 6.92 (s, 2H), 7.49 (t, 1H), 7.65 (m, 1H), 7.74 (t, 1H), 8.02 (d, 1H), 8.38 (d, 1H), 8.46 (d, 1H), 8.51 (d, 1H) 8.77 (s, 1H), 9.10 (s, 1H), 9.21 (s, 1H).

Derivatives of Intermediate 10

Example 26

5-bromo-N[4]-ethyl-2-(4-phenyl-1H-pyrazol-1-yl)pyrimidine-4,6-diamine

HPLC-MS: Rt 4.227 m/z 361.0 (MH$^+$).
$^1$H-NMR (400 MHz, DMSO-$d_6$): δ=1.16 (t, 3H), 3.49 (m, 2H), 6.75 (m, 3H), 7.25 (t, 1H), 7.39 (t, 2H), 7.69 (d, 2H), 8.17 (s, 1H), 8.81 (s, 1H).

Derivatives of Intermediate 11

Example 27

5-bromo-2-[4-(4-chlorophenyl)-1H-pyrazol-1-yl]-N[4]-ethylpyrimidine-4,6-diamine

HPLC-MS: Rt 4.631 m/z 395.0 (MH$^+$).
$^1$H-NMR (400 MHz, DMSO-$d_6$): δ=1.15 (t, 3H), 3.49 (m, 2H), 6.75 (m, 3H), 7.44 (d, 2H), 7.75 (d, 2H), 8.19 (d, 1H), 8.86 (s, 1H).

Example 28

5-bromo-2-[4-(4-chlorophenyl)-1H-pyrazol-1-yl]-N[4]-(prop-2-ynyl)pyrimidine-4,6-diamine HPLC-MS: Rt 4.352 m/z 403.0 (MH$^+$).
$^1$H-NMR (400 MHz, DMSO-$d_6$): δ=3.06 (s, 1H), 4.25 (m, 2H), 6.89 (s, 2H), 7.15 (t, 1H) 7.46 (d, 2H), 7.76 (d, 2H), 8.21 (s, 1H), 8.95 (s, 1H).

Derivatives of Intermediate 12

Example 29

5-bromo-N[4]-[(4-methylthiazol-5-yl)methyl]-2-[4-(pyrazin-2-yl)-1H-pyrazol-1-yl]pyrimidine-4,6-diamine HPLC-MS: Rt 2.891 m/z 444.0 (MH$^+$).
$^1$H-NMR (400 MHz, DMSO-$d_6$): δ=2.46 (s, 3H), 4.78 (d, 2H), 6.93 (s, 2H), 7.55 (t, 1H), 8.39 (s, 1H), 8.48 (d, 1H), 8.63 (s, 1H), 8.76 (s, 1H), 9.13 (d, 1H), 9.17 (s, 1H).

Example 30

5-bromo-N[4]-(prop-2-ynyl)-2-[4-(pyrazin-2-yl)-1H-pyrazol-1-yl]pyrimidine-4,6-diamine HPLC-MS: Rt 2.878 m/z 371.0 (MH$^+$).
$^1$H-NMR (400 MHz, DMSO-$_6$): δ=3.06 (s, 1H), 4.23 (d, 2H), 6.94 (s, 2H), 7.21 (t, 1H), 8.39 (s, 1H), 8.49 (d, 1H), 8.62 (s, 1H), 9.15 (d, 1H), 9.17 (s, 1H).

Derivatives of Intermediate 13

Example 31

5-bromo-N[4]-(prop-2-ynyl)-2-(1H-pyrazolo[3,4-b]pyridin-1-yl)pyrimidine-4,6-diamine HPLC-MS: Rt 2.889 m/z 344.0 (MH$^+$).
$^1$H-NMR (400 MHz, DMSO-$d_6$): δ=3.08 (s, 1H), 4.22 (d, 2H), 7.14 (s, 2H), 7.19 (t, 1H), 7.65 (t, 1H), 8.27 (m, 1H), 8.69 (d, 1H), 9.17 (s, 1H).

Example 32

5-bromo-N[4]-[(4-methylthiazol-5-yl)methyl]-2-(1H-pyrazolo[3,4-b]pyridin-1-yl)pyrimidine-4,6-diamine HPLC-MS: Rt 2.874 m/z 418.0 (MH$^+$).
$^1$H-NMR (400 MHz, DMSO-$d_6$): δ=2.47 (s, 3H), 4.80 (d, 2H), 7.15 (m, 3H), 7.65 (t, 1H), 8.27 (m, 1H), 8.69 (d, 1H), 8.75 (s, 1H), 9.18 (s, 1H).

Intermediate Derivatives 14

Example 33

5-bromo-N[4]-(prop-2-ynyl)-2-(1H-pyrazolo[3,4-c]pyridin-1-yl)pyrimidine-4,6-diamine HPLC-MS: Rt 2.710 m/z 344.0 (MH$^+$).

¹H-NMR (400 MHz, DMSO-d₆): δ=3.08 (s, 1H), 4.23 (t, 2H), 7.00 (s, 2H), 7.27 (t, 1H), 7.84 (d, 1H), 8.40 (d, 1H), 8.47 (s, 1H), 10.15 (s, 1H).

Example 34

5-bromo-N⁴-[(4-methylthiazol-5-yl)methyl]-2-(1H-pyrazolo[3,4-c]pyridin-1-yl)pyrimidine-4,6-diamine HPLC-MS: Rt 2.794 m/z 417.0 (MH⁺).
¹H-NMR (400 MHz, DMSO-d₆): δ=2.47 (s, 3H), 4.80 (d, 2H), 7.01 (s, 2H), 7.57 (t, 1H), 7.84 (d, 1H), 8.40 (d, 1H), 8.47 (s, 1H), 10.0 (s, 1H), 10.16 (s, 1H).

Example 35

5-bromo-N⁴-(cyclopropylmethyl)-2-(1H-pyrazolo[3,4-c]pyridin-1-yl)pyrimidine-4,6-diamine HPLC-MS: Rt 3.349 m/z 362.0 (MH⁺).
¹H-NMR (400 MHz, DMSO-d₆): δ=0.32 (m, 2H), 0.41 (m, 2H), 1.18 (m, 1H) 3.35 (m, 2H), 6.87 (s, 2H) 7.01 (t, 1H), 7.85 (d, 1H), 8.39 (d, 1H) 8.46 (s, 1H), 10.09 (s, 1H).

Example 36

5-bromo-2-(1H-pyrazolo[3,4-c]pyridin-1-yl)-N⁴-[(thiazol-5-yl)methyl]pyrimidine-4,6-diamine HPLC-MS: Rt 2.682 m/z 403.0 (MH⁺).
¹H-NMR (400 MHz, DMSO-d₆): δ=4.87 (d, 2H), 7.03 (s, 2H), 7.56 (t, 1H), 7.84 (d, 1H), 7.89 (s, 1H), 8.40 (d, 1H), 8.50 (s, 1H), 8.86 (s, 1H), 10.05 (s, 1H).

Example 37

5-bromo-N⁴-(2-methoxyethyl)-2-(1H-pyrazolo[3,4-c]pyridin-1-yl)pyrimidine-4,6-diamine HPLC-MS: Rt 2.824 m/z 366.0 (MH⁺).
¹H-NMR (400 MHz, DMSO-d₆): δ=3.28 (s, 3H), 3.54 (t, 2H), 3.65 (m, 2H), 6.70 (t, 1H), 6.93 (s, 2H), 7.85 (d, 1H), 8.40 (d, 1H), 8.46 (s, 1H), 10.05 (s, 1H).

Derivatives of Intermediate 15

Example 38

5-bromo-N⁴-(prop-2-ynyl)-2-(1H-pyrazolo[4,3-c]pyridin-1-yl)pyrimidine-4,6-diamine HPLC-MS: Rt 2.707 m/z 346.0 (MH⁺).
¹H-NMR (400 MHz, DMSO-d₆): δ=3.08 (s, 1H), 4.23 (d, 2H), 6.97 (s, 2H), 7.28 (t, 1H), 8.43 (d, 1H), 8.53 (s, 1H), 8.62 (d, 1H), 9.14 (s, 1H).

Example 39

5-bromo-N⁴-[(4-methylthiazol-5-yl)methyl]-2-(1H-pyrazolo[4,3-c]pyridin-1-yl)pyrimidine-4,6-diamine HPLC-MS: Rt 2710 m/z 417.0 (MH⁺).
¹H-NMR (400 MHz, DMSO-d₆): δ=2.45 (s, 3H), 4.78 (d, 2H), 6.98 (s, 2H), 7.56 (t, 1H), 8.43 (d, 1H), 8.53 (s, 1H), 8.62 (d, 1H), 8.72 (s, 1H), 9.15 (s, 1H).

Derivatives of Intermediate 16

Example 40

5-bromo-N⁴-(prop-2-ynyl)-2-(1H-pyrazolo[4,3-b]pyridin-1-yl)pyrimidine-4,6-diamine HPLC-MS: Rt 2.897 m/z 346.0 (MH⁺).
¹H-NMR (400 MHz, DMSO-d₆): δ=3.08 (s, 1H), 4.23 (d, 2H), 6.91 (s, 2H), 7.29 (t, 1H), 7.54 (m, 1H), 8.54 (d, 1H), 8.60 (s, 1H), 8.71 (d, 1H).

Example 41

5-bromo-N⁴-[(4-methylthiazol-5-yl)methyl]-2-(1H-pyrazolo[4,3-b]pyridin-1-yl)pyrimidine-4,6-diamine HPLC-MS: Rt 2.847 m/z 417.0 (MH⁺).
¹H-NMR (400 MHz, DMSO-d₆): δ=2.45 (s, 3H), 4.78 (d, 2H), 6.92 (s, 2H), 7.45 (t, 1H), 7.54 (m, 1H), 8.54 (d, 1H), 8.60 (s, 1H), 8.72 (d, 1H), 8.87 (s, 1H).

Derivatives of Intermediate 17

Example 42

5-bromo-N⁴-(prop-2-ynyl)-2-(1H-1,2,4-triazol-1-yl)pyrimidine-4,6-diamine

HPLC-MS: Rt 2.307 m/z 296.0 (MH⁺).
¹H-NMR (400 MHz, DMSO-d₆): δ=3.03 (s, 1H), 4.18 (d, 2H), 7.02 (s, 2H), 7.27 (t, 1H), 8.17 (s, 1H), 9.22 (s, 1H).

Example 43

5-bromo-N⁴-[(4-methylthiazol-5-yl)methyl]-2-(1H-1,2,4-triazol-1-yl)pyrimidine-4,6-diamine HPLC-MS: Rt 2.454 m/z 367.0 (MH⁺).
¹H-NMR (400 MHz, DMSO-d₆): δ=2.43 (s, 3H), 4.73 (d, 2H) 7.01 (s, 2H), 7.62 (t, 1H), 8.18 (s, 1H), 8.75 (s, 1H), 9.23 (s, 1H).

Example 44

5-bromo-N⁴-(2-methoxyethyl)-2-(1H-1,2,4-triazol-1-yl)pyrimidine-4,6-diamine

HPLC-MS: Rt 2.307 m/z 316.0 (MH⁺).
¹H-NMR (400 MHz, DMSO-d₆): δ=3.31 (s, 3H), 3.48 (t, 2H), 3.58 (m, 2H), 6.75 (t, 1H), 6.92 (s, 2H), 8.15 (s, 1H), 9.17 (s, 1H).

Example 45

5-bromo-N⁴-[(thiazol-5-yl)methyl]-2-(1H-1,2,4-triazol-1-yl)pyrimidine-4,6-diamine HPLC-MS: Rt 2.265 m/z 353.0 (MH⁺).
¹H-NMR (400 MHz, DMSO-d₆): δ=4.73 (d, 2H), 7.01 (s, 2H), 7.62 (t, 1H), 7.87 (s, 1H), 8.18 (s, 1H), 8.88 (s, 1H), 9.28 (s, 1H).

Example 46

5-bromo-N⁴-(cyclopropylmethyl)-2-(1H-1,2,4-triazol-1-yl)pyrimidine-4,6-diamine

HPLC-MS: Rt 3.016 m/z 312.0 (MH⁺).

$^1$H-NMR (400 MHz, DMSO-$d_6$): δ=0.28 (m, 2H), 0.38 (m, 2H), 1.11 (m, 1H), 3.27 (m, 2H), 6.88 (s, 2H), 6.93 (t, 1H), 8.15 (s, 1H), 9.15 (s, 1H).

Intermediate Derivatives 18

Example 47

1-[4-amino-5-bromo-6-(prop-2-ynylamino)pyrimidin-2-yl]-1H-pyrazole-4-carboxylic acid The ethyl 1-[4-amino-5-bromo-6-(prop-2-ynylamino)pyrimidin-2-yl]-1H-pyrazole-4-carboxylate was obtained using the procedure described for example 1, but starting from ethyl 1-(4-amino-5-bromo-6-chloropyrimidin-2-yl)-1H-pyrazole-4-carboxylate (intermediate 18) and propargylamine. The ester was hydrolyzed with 1 M sodium hydroxide (10 eq.). The resulting sodium salt solution was extracted three times with 10 ml of DCM to remove organic impurities. The aqueous phase was acidified with 4 M HCl, the precipitate was filtered, washed several times with cold water and dried.

HPLC-MS: Rt 1.313 m/z 337.0 (MH$^+$).
$^1$H-NMR (400 MHz, DMSO-$d_6$): δ=3.04 (s, 1H), 4.16 (d, 2H), 6.96 (s, 2H), 7.25 (t, 1H), 8.02 (s, 1H), 8.86 (s, 1H), 12.71 (s, 1H).

The following acids of examples of 48 and 52 were synthesized using the procedure described for example 47, but starting from the corresponding esters:

Example 48

1-[4-amino-5-bromo-6-(ethylamino)pyrimidin-2-yl]-1H-pyrazole-4-carboxylic acid

HPLC-MS: Rt 1.660 m/z 329.0 (MH$^+$).
$^1$H-NMR (400 MHz, DMSO-$d_6$): δ=1.13 (t, 3H), 3.43 (m, 2H), 6.81 (s, 2H), 6.85 (t, 1H), 8.00 (s, 1H), 8.78 (s, 1H), 12.69 (s, 1H).

Example 49

1-{4-[(4-methylthiazol-5-yl)methylamino]-6-amino-5-bromopyrimidin-2-yl}-1H-pyrazole-4-carboxylic acid HPLC-MS: Rt 1.815 m/z 410.0 (MH$^+$).
$^1$H-NMR (400 MHz, DMSO-$d_6$): δ=2.44 (s, 3H), 4.72 (d, 2H), 6.95 (s, 2H), 7.58 (t, 1H), 8.02 (s, 1H), 8.76 (s, 1H), 8.86 (s, 1H), 12.71 (s, 1H).

Example 50

1-[4-(2-methoxyethylamino)-6-amino-5-bromopyrimidin-2-yl]-1H-pyrazole-4-carboxylic acid HPLC-MS: Rt 1.652 m/z 357.0 (MH$^+$).

Example 51

1-[4-amino-5-bromo-6-(cyclopropylmethylamino)pyrimidin-2-yl]-1H-pyrazole-4-carboxylic acid HPLC-MS: Rt 2.240 m/z 355.0 (MH$^+$).

Example 52

1-[4-amino-5-bromo-6-(isopropylamino)pyrimidin-2-yl]-1H-pyrazole-4-carboxylic acid HPLC-MS: Rt 2.180 m/z 343.0 (MH$^+$).

Example 53

{1-[4-amino-5-bromo-6-(ethylamino)pyrimidin-2-yl]-1H-pyrazole-4-yl}(morpholino)methanone A mixture of 50 mg (0.15 mmol) of 1-[4-amino-5-bromo-6-(ethylamino)pyrimidin-2-yl]-1H-pyrazole-4-carboxylic acid (example 48), 15 µl (0.17 mmol) of morpholine, 32 µl (0.23 mmol) of triethylamine and 64 mg (0.17 mmol) of HATU in 1 ml of acetonitrile was stirred at room temperature for 10 min. The formed precipitate was filtered, washed with cold water and dried. 39 mg (64.4%) of a white solid were obtained.

HPLC-MS: Rt 2.787 m/z 398.0 (MH$^+$).
$^1$H-NMR (400 MHz, DMSO-$d_6$): δ=1.13 (t, 3H), 3.43 (m, 2H), 3.60 (s, 8H), 6.78 (s, 2H), 6.82 (t, 1H), 7.91 (s, 1H), 8.64 (s, 1H).

Derivatives of Intermediate 25

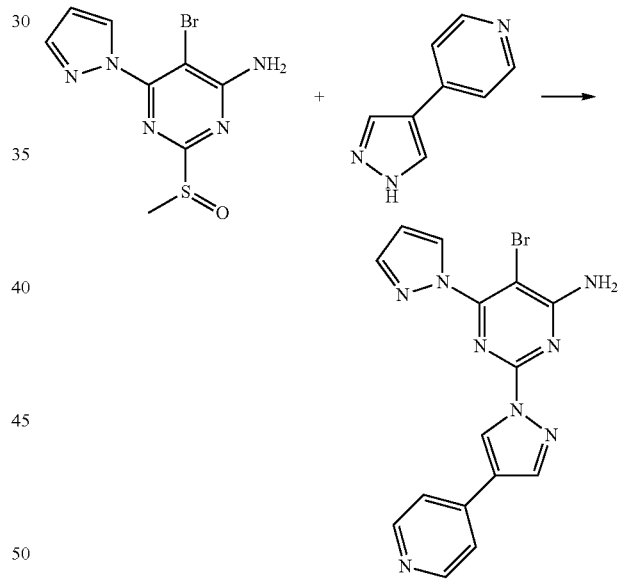

Example 54

5-bromo-6-(1H-pyrazol-1-yl)-2-[4-(pyridin-4-yl)-1H-pyrazol-1-yl]pyrimidine-4-amine A mixture of 0.1 g (0.33 mmol) of 5-bromo-2-(methylsulfinyl)-6-(1H-pyrazol-1-yl)pyrimidine-4-amine (intermediate 25), 0.05 g (0.33 mmol) of 4-(1H-pyrazol-4-yl)pyridine and 0.06 g (0.2 mmol) of Cs$_2$CO$_3$ in 0.5 ml of DMSO was stirred at room temperature for 2 hours. The reaction mixture was poured onto 20 ml of cold water. The formed white precipitate was filtered, washed several times with water and dried. 0.082 g (64.4%) of a white solid were obtained.

HPLC-MS: Rt 2.899 m/z 384.0 (MH+).
¹H-NMR (400 MHz, DMSO-d₆): δ=6.62 (t, 1H), 7.58 (s, 1H), 7.78 (d, 2H), 7.89 (d, 1H), 8.45 (s, 1H), 8.47 (s, 1H), 8.57 (d, 2H), 8.66 (d, 1H), 9.26 (s, 1H).

Compounds of examples from 55 to 59 were synthesized using the procedure described for example 54 but starting from 5-bromo-2-(methylsulfinyl)-6-(1H-pyrazol-1-yl)pyrimidine-4-amine (intermediate 25) and the corresponding pyrazoles or amines:

Example 55

5-bromo-6-(1H-pyrazol-1-yl)-2-[4-(pyridin-2-yl)-1H-pyrazol-1-yl]pyrimidin-4-amine HPLC-MS: Rt 3.207 m/z 385.0 (MH+).
¹H-NMR (400 MHz, DMSO-d₆): δ=6.61 (t, 1H), 7.26 (t, 1H), 7.57 (s, 1H), 7.82 (t, 1H), 7.87 (m, 2H), 8.37 (s, 1H), 8.42 (s, 1H), 8.56 (d, 1H), 8.58 (d, 1H), 9.13 (s, 1H).

Example 56

5-bromo-2-[4-(pyrazin-2-yl)-1H-pyrazol-1-yl]-6-(1H-pyrazol-1-yl)pyrimidine-4-amine HPLC-MS: Rt 2.919 m/z 384.0 (MH+).
¹H-NMR (400 MHz, DMSO-d₆): δ=6.62 (s, 1H), 7.59 (s, 1H), 7.88 (s, 1H), 8.45 (s, 1H), 8.51 (s, 1H), 8.53 (s, 1H), 8.62 (m, 2H), 9.20 (s, 1H), 9.29 (s, 1H).

Example 57

5-bromo-6-(1H-pyrazol-1-yl)-2-(1H-1,2,4-triazol-1-yl)pyrimidine-4-amine

HPLC-MS: Rt 2.316 m/z 308.9 (MH+).
¹H-NMR (400 MHz, DMSO-d₆): δ=6.60 (t, 1H), 7.56 (s, 1H), 7.86 (d, 1H), 8.18 (s, 1H), 8.42 (s, 1H), 8.61 (d, 1H), 9.28 (s, 1H).

Example 58

2-(1H-benzo[d]imidazol-1-yl)-5-bromo-6-(1H-pyrazol-1-yl)pyrimidine-4-amine (not within the scope of the invention)

HPLC-MS: Rt 3.640 m/z 358.0 (MH+).

Example 59

5-bromo-2-(1H-indol-1-yl)-6-(1H-pyrazol-1-yl)pyrimidine-4-amine (not within the Scope of the Invention)

HPLC-MS: Rt 3.679 m/z 356.0 (MH+).

Derivatives of Intermediate 24

Examples from 60 to 62 were synthesized using the procedure described for example 54 but starting from 5-bromo-N⁴-ethyl-2-(methylsulfinyl)pyrimidine-4,6-diamine (intermediate 24) and the corresponding pyrazoles:

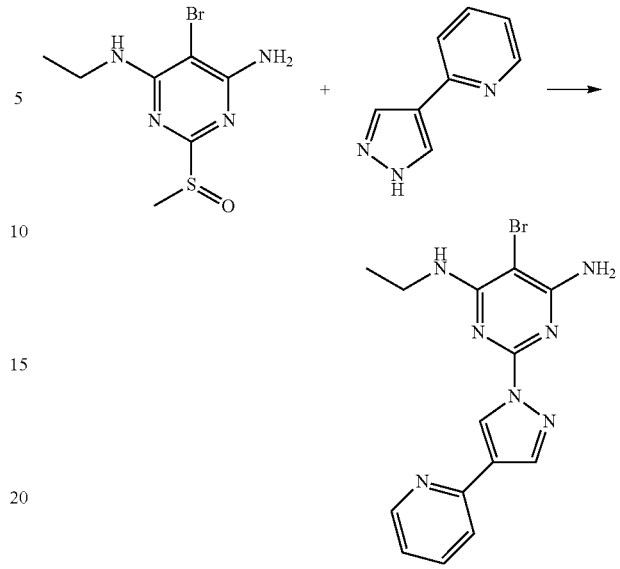

Example 60

5-bromo-N⁴-ethyl-2-[4-(pyridin-2-yl)-1H-pyrazol-1-yl]pyrimidine-4,6-diamine

HPLC-MS: Rt 3.440 m/z 360.0 (MH+).
¹H-NMR (400 MHz, DMSO-d₆): δ=1.16 (t, 3H), 3.48 (m, 2H), 6.76 (s, 2H), 6.78 (t, 1H), 7.24 (t, 1H), 7.81 (m, 2H), 8.28 (s, 1H), 8.56 (d, 1H), 8.96 (s, 1H).

Example 61

5-bromo-N⁴-ethyl-2-[4-(pyrimidin-4-yl)-1H-pyrazol-1-yl]pyrimidine-4,6-diamine

HPLC-MS: Rt 2.924 m/z 363.0 (MH+).
¹H-NMR (400 MHz, DMSO-d₆): δ=1.16 (t, 3H), 3.48 (m, 2H), 6.83 (m, 3H), 7.94 (d, 1H), 8.40 (s, 1H), 8.76 (d, 1H), 9.11 (s, 1H), 9.14 (s, 1H).

Example 62

5-bromo-N⁴-ethyl-2-[4-(quinolin-2-yl)-1H-pyrazol-1-yl]pyrimidine-4,6-diamine

HPLC-MS: Rt 4.308 m/z 410.0 (MH+).
¹H-NMR (400 MHz, DMSO-d₆): δ=1.18 (t, 3H), 3.51 (m, 2H), 6.79 (m, 3H), 7.54 (t, 1H), 7.73 (t, 1H), 7.94 (d, 1H), 7.99 (d, 1H), 8.02 (d, 1H), 8.38 (d, 1H), 8.44 (s, 1H), 9.15 (s, 1H).

Derivatives of Intermediate 26

Examples from 63 to 65 were synthesized using the procedure described for example 54 but starting from 5-chloro-N⁴-ethyl-2-(methylsulfinyl)pyrimidine-4,6-diamine (intermediate-26) and the corresponding pyrazoles:

Example 63

5-chloro-N⁴-ethyl-2-[4-(pyridin-2-yl)-1H-pyrazol-1-yl]pyrimidine-4,6-diamine

HPLC-MS: Rt 3.351 m/z 316.0 (MH+).

$^1$H-NMR (400 MHz, DMSO-d$_6$): δ=1.16 (t, 3H), 3.47 (m, 2H), 6.80 (s, 2H), 6.94 (t, 1H), 7.23 (s, 1H), 7.81 (m, 2H), 8.27 (s, 1H), 8.55 (d, 1H), 8.95 (s, 1H).

Example 64

5-chloro-N$^4$-ethyl-2-(1H-indazol-1-yl)pyrimidine-4,6-diamine

HPLC-MS: Rt 3,964 m/z 289.0 (MH$^+$).
$^1$H-NMR (400 MHz, DMSO-d$_6$): δ=1.20 (t, 3H), 3.51 (m, 2H), 6.78 (s, 1H), 6.90 (s, 1H), 7.08 (m, 1H), 7.27 (m, 1H), 7.51 (m, 1H), 7.83 (d, 1H), 8.30 (s, 1H), 8.69 (d, 1H).

Example 65

5-chloro-N$^4$-ethyl-2-(5-fluoro-1H-indazol-1-yl)pyrimidine-4,6-diamine

HPLC-MS: Rt 4.142 m/z 307.0 (MH$^+$).
$^1$H-NMR (400 MHz, DMSO-d$_6$): δ=1.18 (t, 3H), 3.49 (m, 2H), 6.91 (s, 2H), 7.21 (t, 1H), 7.53 (m, 1H), 7.83 (d, 1H), 8.29 (s, 1H), 8.71 (m, 1H).

Derivatives of Intermediate 33

Example 66

5-bromo-N$^4$-ethyl-2-(1H-indazol-1-yl)-N$^6$-(prop-2-ynyl)pyrimidine-4,6-diamine A mixture of 0.1 g (0.28 mmol) of 5-bromo-6-chloro-2-(1H-indazol-1-yl)-N-(prop-2-ynyl)pyrimidin-4-amine (intermediate 33), 1 mL (excess) of ethylamine 70% in water and 0.065 g (0.2 mmol) of Cs$_2$CO$_3$ in 3 ml of acetonitrile was stirred at 80° C. for 8 hours. The reaction mixture was poured onto 20 ml of cold water. The formed white precipitate was filtered, washed several times with water and dried. 0.064 g (62.3%) were obtained as a white solid.
HPLC-MS: Rt 4.508 m/z 373.0 (MH$^+$).
Examples from 67 to 69 were synthesized using the procedure described for example 66 but starting from 5-bromo-6-chloro-2-(1H-indazol-1-yl)-N-(prop-2-ynyl)pyrimidin-4-amine (intermediate 33), and 4 equivalents of the corresponding amines:

Example 67

5-bromo-N$^4$-(cyclopropylmethyl)-2-(1H-indazol-1-yl)-N$^6$-(prop-2-ynyl)pyrimidine-4,6-diamine HPLC-MS: Rt 4.885 m/z 397.0 (MH$^+$).

Example 68

5-bromo-N$^4$-(tetrahydro-2H-pyran-4-yl)-2-(1H-indazol-1-yl)-N$^6$-(prop-2-ynyl)pyrimidine-4,6-diamine HPLC-MS: Rt 4.366 m/z 428.0 (MH$^+$).
$^1$H-NMR (400 MHz, DMSO-d$_6$): δ=1.72 (m, 2H), 1.83 (m, 2H), 3.08 (s, 1H), 3.43 (m, 2H), 3.90 (m, 2H), 4.24 (m, 3H), 6.40 (d, 1H), 7.17 (t, 1H), 7.29 (t, 1H), 7.73 (m, 1H), 7.85 (d, 1H), 8.38 (s, 1H), 8.71 (d, 1H).

Example 69

N$^4$-[(1H-benzo[d]imidazol-2-yl)methyl]-5-bromo-2-(1H-indazol-1-yl)-N$^6$-(prop-2-ynyl)pyrimidine-4,6-diamine HPLC-MS: Rt 4.927 m/z 474.1 (MH$^+$).

Derivatives of Intermediate 34

Examples from 70 to 73 were synthesized using the procedure described for example 66 but starting from 5-bromo-6-chloro-N-(prop-2-ynyl)-2-[4-(pyridin-2-yl)-1H-pyrazol-1-yl]pyrimidin-4-amine (intermediate 34), and the corresponding amines:

Example 70

5-bromo-N$^4$-ethyl-N$^6$-(prop-2-ynyl)-2-[4-(pyridin-2-yl)-1H-pyrazol-1-yl]pyrimidine-4,6-diamine HPLC-MS: Rt 4.018 m/z 398.0 (MH$^+$).
$^1$H-NMR (400 MHz, DMSO-d$_6$): δ=1.16 (t, 3H), 3.05 (s, 1H), 3.49 (q, H, 2), 4.22 (d, 2H), 6.85 (t, 1H), 7.11 (t, 1H), 7.24 (t, 1H), 7.81 (t, 1H), 7.84 (t, 1H), 8.32 (s, 1H), 8.57 (d, 1H), 9.05 (s, 1H).

Example 71

5-bromo-N$^4$-(cyclopropylmethyl)-N$^6$-(prop-2-ynyl)-2-[4-(pyridin-2-yl)-1H-pyrazol-1-yl]pyrimidine-4,6-diamine HPLC-MS: Rt 4.369 m/z 426.0 (MH$^+$).
$^1$H-NMR (400 MHz, DMSO-d$_6$): δ=0.32 (m, 2H), 0.41 (m, 2H), 1.14 (m, 1H), 3.05 (s, 1H), 3.32 (t, 2H), 4.23 (d, 2H), 6.90 (t, 1H), 7.13 (t, 1H), 7.24 (t, 1H), 7.81 (t, 1H), 7.83 (t, 1H), 8.32 (s, 1H), 8.57 (d, 1H), 9.05 (s, 1H).

Example 72

5-bromo-N$^4$-(tetrahydro-2H-pyran-4-yl)-N$^6$-(prop-2-ynyl)-2-[4-(pyridin-2-yl)-1H-pyrazol-1-yl]pyrimidine-4,6-diamine HPLC-MS: Rt 3.795 m/z 456.0 (MH$^+$).
$^1$H-NMR (400 MHz, DMSO-d$_6$): δ=1.68 (m, 2H), 1.78 (m, 2H), 3.06 (s, 1H), 3.42 (t, 2H), 3.88 (m, 2H), 4.23 (m, 2H), 4.28 (m, 1H), 6.43 (d, 1H), 7.17 (t, 1H), 7.25 (t, 1H), 7.81 (d, 1H), 7.83 (t, 1H), 8.33 (s, 1H), 8.57 (d, 1H), 9.04 (s, 1H).

Example 73

N$^4$-[(1H-benzo[d]imidazol-2-yl)methyl]-5-bromo-N$^6$-(prop-2-ynyl)-2-[4-(pyridin-2-yl)-1H-pyrazol-1-yl]pyrimidine-4,6-diamine HPLC-MS: Rt 4.123 m/z 501.1 (MH$^+$).

Derivatives of Intermediate 35

Examples from 74 to 77 were synthesized using the procedure described for example 66 but starting from 5-bromo-6-chloro-N-ethyl-2-[4-(pyrimidin-4-yl)-1H-pyrazol-1-yl]pyrimidin-4-amine (intermediate 35), and the corresponding amines:

Example 74

5-bromo-$N^4$-ethyl-$N^6$-(prop-2-ynyl)-2-[4-(pyrimidin-4-yl)-1H-pyrazol-1-yl]pyrimidine-4,6-diamine HPLC-MS: Rt 3.528 m/z 399.0 (MH$^+$).
$^1$H-NMR (400 MHz, DMSO-d$_6$): δ=1.15 (m, 2H), 3.05 (s, 1H), 3.49 (m, 2H), 3.90 (m, 2H), 4.23 (d, 2H), 6.89 (t, 1H), 7.15 (t, 1H), 7.97 (d, 1H), 8.44 (s, 1H), 8.77 (d, 1H), 9.13 (s, 1H), 9.24 (s, 1H).

Example 75

5-bromo-$N^4$-(cyclopropylmethyl)-$N^6$-ethyl-2-[4-(pyrimidin-4-yl)-1H-pyrazol-1-yl]pyrimidine-4,6-diamine HPLC-MS: Rt 4.176 m/z 417.0 (MH$^+$).
$^1$H-NMR (400 MHz, DMSO-d$_6$): δ=0.30 (m, 2H), 0.40 (m, 2H), 1.12 (m, 1H), 1.15 (t, 3H), 3.31 (t, 2H), 3.49 (m, 2H), 6.76 (d, 1H), 6.78 (d, 1H), 7.97 (d, 1H), 8.42 (s, 1H), 8.76 (d, 1H), 9.12 (s, 1H), 9.18 (s, 1H).

Example 76

5-bromo-$N^4$-ethyl-$N^6$-(tetrahydro-2H-pyran-4-yl)-2-[4-(pyrimidin-4-yl)-1H-pyrazol-1-yl]pyrimidine-4,6-diamine HPLC-MS: Rt 3.589 m/z 445.1 (MH$^+$).
$^1$H-NMR (400 MHz, DMSO-d$_6$): δ=1.15 (t, 3H), 1.68 (m, 2H), 1.78 (m, 2H), 3.42 (m, 2H), 3.48 (m, 2H), 3.86 (m, 2H), 4.26 (m, 1H), 6.32 (d, 1H), 6.81 (t, 1H), 7.97 (d, 1H), 8.43 (s, 1H), 8.77 (d, 1H), 9.12 (s, 1H), 9.17 (s, 1H).

Example 77

$N^4$-[(1H-benzo[d]imidazol-2-yl)methyl]-5-bromo-$N^6$-ethyl-2-[4-(pyrimidin-4-yl)-1H-pyrazol-1-yl]pyrimidine-4,6-diamine HPLC-MS: Rt 3.822 m/z 493.1 (MH$^+$).
$^1$H-NMR (400 MHz, DMSO-d$_6$): δ=1.20 (t, 3H), 3.56 (m, 2H), 4.82 (d, 2H), 6.89 (t, 1H), 7.15 (t, 1H), 7.97 (d, 1H), 8.01 (d, 1H), 8.03 (d, 1H), 8.49 (s, 1H), 8.77 (d, 1H), 8.79 (d, 1H), 9.13 (d, 1H), 9.24 (s, 1H).

The invention claimed is:
1. Compound of formula (I):

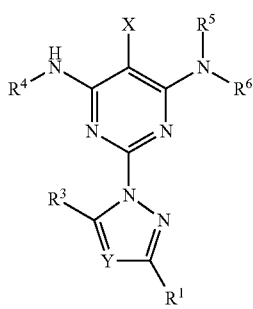

wherein:
$R^1$ is selected from the group consisting of hydrogen, halogen, cycloalkyl and alkyl of three or four carbon atoms, linear or branched;
Y is selected from the group consisting of C—$R^2$ and a nitrogen atom;
$R^2$ is selected from the group consisting of:
(a) aryl or heteroaryl group optionally substituted by one or more halogen atoms, or by one or more, cycloalkyl, hydroxy, ($C_1$-$C_8$) alkoxy, ($C_1$-$C_8$) alkylthio, amino, mono- or dialkylamino, alkoxyalkyl, hydroxycarbonyl and alkoxycarbonyl groups,
(b) a group of formula (—CO($R^7$)), where $R^7$ represents a hydroxyl group or a [—N($R^8$)($R^9$)] group;
$R^8$ and $R^9$ are independently selected from the group consisting of hydrogen atom, cycloalkyl and alkyl of three or four carbon atoms, linear or branched and optionally substituted by halogen or an aryl or heterocyclic group; or $R^8$ and $R^9$ form, together with the nitrogen atom to which they are attached a saturated five- or six-membered ring which optionally comprises a further heteroatom selected from the group consisting of oxygen and nitrogen optionally substituted by a ($C_1$-$C_8$) alkyl group;
$R^3$ is selected from the group consisting of hydrogen, halogen, cycloalkyl group and a ($C_1$-$C_8$) alkyl group, linear or branched optionally substituted by halogen atoms;
or $R^2$ and $R^3$ form, together with the carbon atoms to which they are attached, an six-membered aryl or heteroaryl ring optionally substituted by one or more halogen atoms, or by one or more groups selected from cycloalkyl, hydroxy, ($C_1$-$C_8$) alkoxy, ($C_1$-$C_8$) alkylthio, amino, mono- or dialkylamino, alkoxyalkyl, hydroxycarbonyl and alkoxycarbonyl;
X is selected from the group consisting of halogen atom and cyano group;
$R^4$ and $R^5$ are independently selected from the group consisting of:
(a) a hydrogen atom;
(b) an alkyl, cycloalkyl or cycloalkylalkyl group having a maximum of five carbon atoms, linear or branched, optionally substituted by one or more halogen atoms, methoxy groups, or heteroaryl group, said heteroaryl group being optionally substituted with halogen atoms or ($C_1$-$C_8$) alkyl groups;
(c) an allyl or propargyl group optionally substituted by one or more halogen atoms or by one or more groups selected from the group consisting of cycloalkyl, hydroxy, ($C_1$-$C_8$) alkoxy, ($C_1$-$C_8$) alkylthio, amino, mono- or dialkylamino, alkoxyalkyl, hydroxycarbonyl and alkoxycarbonyl; and
(d) a tetrahydropyranyl group;
$R^6$ is selected from the group consisting of:
(a) an alkyl group having a maximum of five carbon atoms, linear or branched, substituted by heteroaryl group, said heteroaryl group being optionally substituted with halogen atoms or ($C_1$-$C_8$) alkyl groups;
(b) an allyl or propargyl group optionally substituted by one or more halogen atoms or by one or more groups selected from the group consisting of cycloalkyl, hydroxy, ($C_1$-$C_8$) alkoxy, ($C_1$-$C_8$) alkylthio, amino, mono- or dialkylamino, alkoxyalkyl, hydroxycarbonyl and alkoxycarbonyl; and
(c) a tetrahydropyranyl group;
and pharmaceutically acceptable salts thereof.

2. The compound according to claim 1, wherein $R^4$ is a hydrogen atom.

3. The compound according to claim 2, wherein $R^1$, $R^3$ and $R^5$ are a hydrogen atom, X is a bromine atom and Y is a nitrogen atom.

4. The compound according to claim 3, wherein $R^6$ is selected from the group consisting of ($C_1$-$C_5$) alkyl substituted with a heteroaryl group, which in turn can be optionally substituted by a ($C_1$-$C_8$) alkyl group.

5. The compound according to claim 4, wherein $R^6$ is selected from the group consisting of ethyl and propyl substituted by a five-membered heteroaryl group, which in turn is optionally substituted by one or more methyl groups.

6. The compound according to claim 3, wherein $R^6$ is selected from the group consisting of allyl, propargyl and tetrahydropyranyl, all of them being optionally substituted with an alkyl group, linear or branched, having a maximum of three carbon atoms.

7. The compound according to claim 2, wherein $R^1$, $R^3$ and $R^5$ are a hydrogen atom, X is a bromine atom, Y is a C—$R^2$ moiety and $R^2$ is a heteroaryl group optionally substituted by halogen atoms.

8. The compound according to claim 7, wherein $R^2$ is selected from pyridine, quinoline, pyrimidine or pyrazine, which are optionally substituted by halogen atoms.

9. The compound according to claim 8, wherein $R^6$ is selected from the group consisting of ($C_1$-$C_5$) alkyl substituted with a heteroaryl group which, in turn, is optionally substituted by a ($C_1$-$C_8$) alkyl group.

10. The compound according to claim 8, wherein $R^6$ is selected from the group consisting of ethyl and propyl substituted by a five-membered heteroaryl group optionally substituted by one or more methyl groups.

11. The compound according to claim 8, wherein $R^6$ is selected from the group consisting of allyl, propargyl and tetrahydropyranyl groups optionally substituted by halogen atoms.

12. The compound according to claim 2, wherein $R^1$ and $R^5$ are a hydrogen atom, X is a bromine atom, Y is a carbon atom and $R^2$ and $R^3$ form, together with the carbon atoms to which they are attached, an optionally substituted aryl or heteroaryl group.

13. The compound according to claim 12, wherein $R^2$ and $R^3$ form, together with the atoms of carbon to which they are attached, a phenyl or pyridine rings optionally substituted by halogen atoms.

14. The compound according to claim 13, wherein $R^6$ is selected from the group consisting of ($C_1$-$C_5$) alkyl substituted by a heteroaryl group which, in turn, is optionally substituted by a ($C_1$-$C_8$) alkyl group.

15. The compound according to claim 14, wherein $R^6$ is selected from the group consisting of ethyl and propyl substituted by a five-membered heteroaryl group optionally substituted by one or more methyl groups.

16. The compound according to claim 13, wherein $R^6$ is selected from the group consisting of optionally substituted allyl, propargyl, and tetrahydropyranyl.

17. The compound according to claim 2, wherein $R^1$ and $R^5$ are a hydrogen atom, X is a bromine atom, Y is a $CR^2$ moiety, $R^2$ and $R^3$ form, together with the carbon atoms to which are attached, a phenyl or pyridine ring and $R^6$ is selected from the group consisting of ethyl and propyl substituted by a thiazole ring, which is optionally substituted by one or more methyl groups.

18. The compound according to claim 2, wherein $R^1$, $R^3$ and $R^5$ are a hydrogen atom, X is a bromine atom, Y is a nitrogen atom, and $R^6$ is selected from the group consisting of:
(a) ethyl and propyl substituted by a thiazole ring, which in turn is optionally substituted by one or more methyl groups; and
(b) propargyl group.

19. A compound according to claim 1, which is selected from the group consisting of:
5-bromo-2-(1H-indazol-1-yl)-$N^4$-(prop-2-ynyl)pyrimidine-4,6-diamine;
$N^4$-[(1H-benzo[d]imidazol-2-yl)methyl]-5-bromo-2-(1H-indazol-1-yl)pyrimidine-4,6-diamine;
5-bromo-2-(1H-indazol-1-yl)-$N^4$-[(2-methylthiazol-4-yl)methyl]pyrimidine-4,6-diamine;
5-bromo-$N^4$-(tetrahydro-2H-pyran-4-yl)-2-(1H-indazol-1-yl)pyrimidine-4,6-diamine;
5-bromo-2-(1H-indazol-1-yl)-$N^4$-[(1-methyl-1H-pyrazol-4-yl)methyl]pyrimidine-4,6-diamine;
5-bromo-2-(1H-indazol-1-yl)-$N^4$-[(thiazol-5-yl)methyl]pyrimidine-4,6-diamine;
5-bromo-2-(1H-indazol-1-yl)-$N^4$-[(4-methylthiazol-5-yl)methyl]pyrimidine-4,6-diamine;
5-bromo-$N^4$-(prop-2-ynyl)-2-[4-(pyridin-4-yl)-1H-pyrazol-1-yl]pyrimidine-4,6-diamine;
5-bromo-2-(4-(pyridin-4-yl)-1H-pyrazol-1-yl)-$N^4$-[(thiazol-5-yl)methyl]pyrimidine-4,6-diamine;
5-bromo-$N^4$-(prop-2-ynyl)-2-[4-(pyridin-2-yl)-1H-pyrazol-1-yl]pyrimidine-4,6-diamine;
5-bromo-$N^4$-[(4-methylthiazol-5-yl)methyl]-2-(4-(pyridin-2-yl)-1H-pyrazol-1-yl)pyrimidine-4,6-diamine;
5-bromo-2-[4-(pyridin-2-yl)-1H-pyrazol-1-yl]-$N^4$-[(thiazol-5-yl)methyl]pyrimidine-4,6-diamine;
5-bromo-$N^4$-(prop-2-ynyl)-2-[4-(quinolin-2-yl)-1H-pyrazol-1-yl]pyrimidine-4,6-diamine;
5-bromo-$N^4$-(tetrahydro-2H-pyran-4-yl)-2-[4-(quinolin-2-yl)-1H-pyrazol-1-yl]pyrimidine-4,6-diamine;
5-bromo-$N^4$-[(2-methylthiazol-4-yl)methyl]-2-[4-(quinolin-2-yl)-1H-pyrazol-1-yl]pyrimidine-4,6-diamine;
5-bromo-$N^4$-[(4-methylthiazol-5-yl)methyl]-2-[4-(quinolin-2-yl)-1H-pyrazol-1-yl]pyrimidine-4,6-diamine;
5-bromo-2-[4-(4-chlorophenyl)-1H-pyrazol-1-yl]-$N^4$-(prop-2-ynyl)pyrimidine-4,6-diamine;
5-bromo-$N^4$-[(4-methylthiazol-5-yl)methyl]-2-[4-(pyrazin-2-yl)-1H-pyrazol-1-yl]pyrimidine-4,6-diamine;
5-bromo-$N^4$-(prop-2-ynyl)-2-[4-(pyrazin-2-yl)-1H-pyrazol-1-yl]pyrimidine-4,6-diamine;
5-bromo-$N^4$-(prop-2-ynyl)-2-(1H-pyrazolo[3,4-b]pyridin-1-yl)pyrimidine-4,6-diamine;
5-bromo-$N^4$-[(4-methylthiazol-5-yl)methyl]-2-(1H-pyrazolo[3,4-b]pyridin-1-yl)pyrimidine-4,6-diamine;
5-bromo-$N^4$-(prop-2-ynyl)-2-(1H-pyrazolo[3,4-c]pyridin-1-yl)pyrimidine-4,6-diamine;
5-bromo-$N^4$-[(4-methylthiazol-5-yl)methyl]-2-(1H-pyrazolo[3,4-c]pyridin-1-yl)pyrimidine-4,6-diamine;
5-bromo-2-(1H-pyrazolo[3,4-c]pyridin-1-yl)-$N^4$-[(thiazol-5-yl)methyl]pyrimidine-4,6-diamine;
5-bromo-$N^4$-(prop-2-ynyl)-2-(1H-pyrazolo[4,3-c]pyridin-1-yl)pyrimidine-4,6-diamine;
5-bromo-$N^4$-[(4-methylthiazol-5-yl)methyl]-2-(1H-pyrazolo[4,3-c]pyridin-1-yl)pyrimidine-4,6-diamine;
5-bromo-$N^4$-(prop-2-ynyl)-2-(1H-pyrazolo[4,3-b]pyridin-1-yl)pyrimidine-4,6-diamine;
5-bromo-$N^4$-[(4-methylthiazol-5-yl)methyl]-2-(1H-pyrazolo[4,3-b]pyridin-1-yl)pyrimidine-4,6-diamine;

5-bromo-$N^4$-(prop-2-ynyl)-2-(1H-1,2,4-triazol-1-yl)pyrimidine-4,6-diamine;
5-bromo-$N^4$-[(4-methylthiazol-5-yl)methyl]-2-(1H-1,2,4-triazol-1-yl)pyrimidine-4,6-diamine;
5-bromo-$N^4$-[(thiazol-5-yl)methyl]-2-(1H-1,2,4-triazol-1-yl)pyrimidine-4,6-diamine;
1-[4-amino-5-bromo-6-(prop-2-ynylamino)pyrimidin-2-yl]-1H-pyrazole-4-carboxylic acid;
5-bromo-$N^4$-ethyl-2-(1H-indazol-1-yl)-$N^6$-(prop-2-ynyl)pyrimidine-4,6-diamine;
5-bromo-$N^4$-(cyclopropylmethyl)-2-(1H-indazol-1-yl)-$N^6$-(prop-2-ynyl)pyrimidine-4,6-diamine;
5-bromo-$N^4$-(tetrahydro-2H-pyran-4-yl)-2-(1H-indazol-1-yl)-$N^6$-(prop-2-ynyl)pyrimidine-4,6-diamine;
$N^4$-[(1H-benzo[d]imidazol-2-yl)methyl]-5-bromo-2-(1H-indazol-1-yl)-$N^6$-(prop-2-ynyl)pyrimidine-4,6-diamine;
5-bromo-$N^4$-ethyl-$N^6$-(prop-2-ynyl)-2-[4-(pyridin-2-yl)-1H-pyrazol-1-yl]pyrimidine-4,6-diamine;
5-bromo-$N^4$-(cyclopropylmethyl)-$N^6$-(prop-2-ynyl)-2-[4-(pyridin-2-yl)-1H-pyrazol-1-yl]pyrimidine-4,6-diamine;
5-bromo-$N^4$-(tetrahydro-2H-pyran-4-yl)-$N^6$-(prop-2-ynyl)-2-[4-(pyridin-2-yl)-1H-pyrazol-1-yl]pyrimidine-4,6-diamine;
$N^4$-[(1H-benzo[d]imidazol-2-yl)methyl]-5-bromo-$N^6$-(prop-2-ynyl)-2-[4-(pyridin-2-yl)-1H-pyrazol-1-yl]pyrimidine-4,6-diamine;
5-bromo-$N^4$-ethyl-$N^6$-(prop-2-ynyl)-2-[4-(pyrimidin-4-yl)-1H-pyrazol-1-yl]pyrimidine-4,6-diamine;
5-bromo-$N^4$-ethyl-$N^6$-(tetrahydro-2H-pyran-4-yl)-2-[4-(pyrimidin-4-yl)-1H-pyrazol-1-yl]pyrimidine-4,6-diamine; and
$N^4$-[(1H-benzo[d]imidazol-2-yl)methyl]-5-bromo-$N^6$-ethyl-2-[4-(pyrimidin-4-yl)-1H-pyrazol-1-yl]pyrimidine-4,6-diamine.

20. Method of treatment of a disease or pathological condition susceptible of improvement by inhibition of Phosphodiesterase 10 selected from the group consisting of schizophrenia, Huntington's disease, Parkinson's disease, Alzheimer's disease, and depression, comprising administering to a subject in need thereof an effective amount of a compound according to claim 1.

21. A combination product that comprises a compound according to claim 1, and at least another drug, said drug being selected from the group consisting of drugs that are useful for the treatment of a disease selected from the group consisting of schizophrenia, Parkinson's disease, Huntington's disease, Alzheimer's disease, and depression.

22. A pharmaceutical composition comprising a compound of claim 1 together with a pharmaceutically acceptable excipient.

23. A method of inhibiting Phosphodiesterase 10 activity in a subject, comprising administering to the subject an effective amount of a compound according to claim 1 wherein the subject has a disease selected from the group consisting of schizophrenia, Parkinson's disease, Huntington's disease, Alzheimer's disease, and depression.

* * * * *

UNITED STATES PATENT AND TRADEMARK OFFICE
CERTIFICATE OF CORRECTION

| | |
|---|---|
| PATENT NO. | : 9,447,095 B2 |
| APPLICATION NO. | : 14/762655 |
| DATED | : September 20, 2016 |
| INVENTOR(S) | : Camacho Gómez et al. |

It is certified that error appears in the above-identified patent and that said Letters Patent is hereby corrected as shown below:

On the Title Page
Item (22) PCT Filed: change "Jan. 24, 2014" to -- Jan. 23, 2014 --

Signed and Sealed this
Third Day of January, 2017

Michelle K. Lee
*Director of the United States Patent and Trademark Office*